(12) United States Patent  
Chen et al.

(10) Patent No.: US 8,364,421 B2  
(45) Date of Patent: Jan. 29, 2013

(54) DOWNHOLE SANDING ANALYSIS TOOL

(75) Inventors: Felix Chen, Newtown, CT (US); Gary Corris, Newtown, CT (US)

(73) Assignee: Schlumberger Technology Corporation, Sugar Land, TX (US)

( * ) Notice: Subject to any disclaimer, the term of this patent is extended or adjusted under 35 U.S.C. 154(b) by 671 days.

(21) Appl. No.: 12/201,859

(22) Filed: Aug. 29, 2008

(65) Prior Publication Data

US 2010/0057378 A1    Mar. 4, 2010

(51) Int. Cl.  
*G06F 19/00* (2011.01)

(52) U.S. Cl. ......... 702/25; 73/61.71; 250/256; 166/312; 166/311; 166/173

(58) Field of Classification Search ............. 702/25; 73/61.71, 61.75, 61.79, 861.42, 152.42, 152.32; 250/269.1, 269.3, 310, 256; 166/312, 311, 166/173, 255.1, 222, 66, 250.01; 175/40, 175/50

See application file for complete search history.

(56) References Cited

U.S. PATENT DOCUMENTS

| | | | | |
|---|---|---|---|---|
| 4,228,353 A * | 10/1980 | Johnson | ............. | 250/356.1 |
| 4,240,287 A | 12/1980 | Mast et al. | | |
| 4,550,768 A | 11/1985 | McMullen et al. | | |
| 4,716,958 A * | 1/1988 | Walters et al. | ............. | 165/142 |
| 4,994,671 A * | 2/1991 | Safinya et al. | ............. | 250/255 |
| 5,257,530 A | 11/1993 | Beattie et al. | | |
| 5,419,176 A | 5/1995 | Walker | | |
| 5,458,198 A * | 10/1995 | Hashemi et al. | ............. | 166/312 |
| 5,594,246 A | 1/1997 | Sudo et al. | | |
| 5,680,431 A * | 10/1997 | Pietras et al. | ............. | 378/119 |
| 5,789,662 A | 8/1998 | Dayal | | |
| 6,062,311 A * | 5/2000 | Johnson et al. | ............. | 166/312 |
| 6,173,771 B1 * | 1/2001 | Eslinger et al. | ............. | 166/173 |
| 6,176,323 B1 * | 1/2001 | Weirich et al. | ............. | 175/40 |
| 6,354,147 B1 | 3/2002 | Gysling et al. | | |
| 6,354,334 B1 * | 3/2002 | Ellyin et al. | ............. | 138/143 |
| 6,691,584 B2 | 2/2004 | Gysling et al. | | |
| 6,782,150 B2 | 8/2004 | David et al. | | |
| 7,075,062 B2 * | 7/2006 | Chen et al. | ............. | 250/269.1 |

(Continued)

FOREIGN PATENT DOCUMENTS

| | | |
|---|---|---|
| EP | 0269432 | 9/1994 |
| JP | 05332959 | 12/1993 |

(Continued)

OTHER PUBLICATIONS

Coulthard, et al. "Non-restrictive measurement of solids mass flowrate in pneumatic conveying systems", School of Science and Technology, Teesside Polytechnic, May 1991, 7 pages.

(Continued)

*Primary Examiner* — Carol Tsai  
(74) *Attorney, Agent, or Firm* — Jakub Michna; Rachel E. Greene; Bridget Laffey

(57) ABSTRACT

Methods and devices for detecting particles in a fluid within a medium, such the analyzing device includes: a source adapted to transmit signals into the medium; at least one detector adapted to detect signals transmitted from the source such that the at least one detector and the source are structured and arranged on opposite sides of the medium; at least one processing unit in communication with the at least one detector and adapted to produce a plurality of output signals representative of one of at least one particle characteristic or one or more particle property.

44 Claims, 17 Drawing Sheets

U.S. PATENT DOCUMENTS

| | | | |
|---|---|---|---|
| 7,308,941 B2 * | 12/2007 | Rolovic et al. | 166/312 |
| 7,634,059 B2 * | 12/2009 | Wraight | 378/89 |
| 7,817,781 B2 * | 10/2010 | Wraight et al. | 378/119 |
| 2003/0057366 A1 * | 3/2003 | Gzara et al. | 250/269.3 |
| 2003/0219097 A1 * | 11/2003 | Buijsse | 378/43 |
| 2004/0007059 A1 * | 1/2004 | Tudor | 73/152.42 |
| 2004/0163808 A1 * | 8/2004 | Ringgenberg et al. | 166/250.16 |
| 2005/0126777 A1 * | 6/2005 | Rolovic et al. | 166/255.1 |
| 2007/0175280 A1 | 8/2007 | Johansen | |
| 2007/0189452 A1 | 8/2007 | Johnson et al. | |
| 2008/0028838 A1 | 2/2008 | Andersen et al. | |
| 2008/0066962 A1 * | 3/2008 | Rolovic et al. | 175/50 |
| 2008/0315110 A1 * | 12/2008 | Iwatschenko-Borho et al. | 250/394 |

FOREIGN PATENT DOCUMENTS

| | | |
|---|---|---|
| JP | 6090153 | 11/1994 |
| JP | 10506195 | 6/1998 |
| WO | 9610172 A1 | 4/1996 |
| WO | 2007098328 | 8/2007 |

OTHER PUBLICATIONS

Mennell, et al. "Non-invasive two phase flow measurement using soft x-ray attenuation", The Institute of Electrical Engineers, 1996, 3 pages.

International Search Report of PCT Application Serial No. PCT/US2009/051795 dated Mar. 16, 2010.

International Preliminary Report on Patentability of PCT Application Serial No. PCT/US2009/051795 dated Mar. 1, 2011.

Anonymous, "Clampon DSP Partiacle Monitor," CLAMPON Ultrasonic Intelligent Sensors, ClampOn Inc., Houston, 2000: pp. 1-6.

Merletti et al., "SPE 102444: Accurate Detection and Spatial Delineation of Thin-Sand Sedimentary Sequences via Joint Stochastic Inversion of Well Logs and 3D Pre-Stack Seismic Amplitude Data," SPE International, 2006: pp. 1-17.

Morton, "Screen Out Sand," BP Frontiers, Dec. 2001, vol. 2: pp. 18-22.

* cited by examiner

```
Source, medium & detector
In transmission arrangement
```
→ Non-imaging technique: continuous measurement. Individual sand particle is sensed when it crosses dual sensing beams. →

```
Processing unit records:
# of particles sensed > population
Individual beam blocking time > particle size
Correlation btw signals from dual beam > velocity
```
→

```
Improvement: chopping dual beam improves S/N
of dual beam correlation measurement
```

Fig. 30

DOWNHOLE SANDING ANALYSIS TOOL

BACKGROUND OF THE INVENTION

1. Field of the Invention

The invention generally relates to methods, systems and devices for detecting solid particles in a flowing fluid within a medium.

2. Background of the Invention

Methods and equipment for detecting solid particles in a flowing fluid is known already, where solid particles such as sand grains are often entrained in a flowing fluid that is recovered from an underground formation. For example, sand can cause damage to pipes, pumps, valves, fluid treating installations on the surface, and other related oil production or exploration equipment. Also the production of sand may result in clogged well lines that can result in filling in the well and stopping production. When this clogging occurs, the production of all oil wells feeding into the separator tanks must be stopped. Generally, the presence of sand can be dependent upon how an oil related fluid (such as gas and/or liquid hydrocarbons) was produced and the nature of the production reservoir. It is possible that a significant amount of sand can be present when an oil related fluid is produced from a reservoir. Also, sand can also be present with hydrocarbon fluids when produced in gravel pack operations which are experiencing partial or complete failure. In order to prevent such a costly expense, an early warning system is required to detect the presence of those amounts of sand grains that can be expected to cause damage of the recovery equipment in the well or on the production site.

A known method for detecting individual solid particles carried in a particular flow area of a flowing fluid includes grains impinging on a piezoelectric transducer. The peak value of the resulting electric output signal is detected in a pulse height discriminator after a suitable amplification of this signal. When the peak value exceeds a pre-set discrimination level, a standard output pulse is produced with a length that is greater than the typical duration of the impact signal. The number of standard pulses is counted in a pre-determined period. At a given velocity, the grain diameter can be estimated from the peak amplitude of the impact response, and a differentiation can be made between different ranges of grain sizes which will lead to a grain-size distribution of the grains that pass through a given area of the cross-section of the conduit over a given period (see Background section of U.S. Pat. No. 4,240,287).

Another method for detecting solid particles, such as sand, moving in a flowing fluid includes a sensor that generates signals in response to particle impact (see U.S. Pat. No. 4,240,287). Such a sensor conventionally comprises a piezo-electric element coupled to the sensor housing so that collision of particles with the housing deform the element, causing the latter to generate a voltage signal which may be analyzed to obtain information on the nature of the impact. For example, the signal can be amplified, unwanted frequency components filtered-out and a thresh-holding procedure is then applied in order to determine whether the amplitude of the signal is greater than a pre-determined threshold level. If that threshold is passed, the detection of an impact is registered in a counter.

Because the magnitude of the sensor signal is related to the force of particle impact, a series of different threshold levels may be employed in order to give an indication of the relative magnitudes of particle impacts. The energy dissipated on impact is proportional to the momentum of the particle involved, from which an indication of the mass of the particle can be obtained if the velocity of impact is known (or deduced from, for example, the flow-rate of the fluid). An example of such an arrangement is shown in U.S. Pat. No. 4,240,287. However, one disadvantage of such an arrangement is that an accurate measure of particle size is not obtained, since the various impact signals are merely sorted into a number of ranges dictated by the threshold levels.

Other sand detector methods may include fiber optic sensors and flowmeters which provide for monitor parameters such as fluid sound speed, fluid velocity, pressure, and temperature. Such fiber optic based flowmeters are disclosed in the following U.S. Patents, and are hereby incorporated by reference in their entireties: U.S. Pat. No. 6,782,150, entitled "Apparatus for Sensing Fluid in a Pipe;" U.S. Pat. No. 6,691,584, entitled "Flow Rate Measurements Using Unsteady Pressures;" and U.S. Pat. No. 6,354,147, entitled "Fluid Parameter Measurement in Pipes Using Acoustic Pressures," hereinafter referred to as the "flowmeter references." However, these flowmeter references fail to provide any ability to reliably monitor sand production at the surface or downhole in real-time. At least one disadvantage over the above-note prior art is that sonic techniques generally detect the presence of sand particles, but not other attributes, e.g., grain sizes, velocities, etc., all of which, among other things, are important to assess the potential erosion, for example to oil field applications such as pipes and/or equipment. Further, sonic techniques are also not sensitive, if at all, when the sand population is low.

Therefore, there exists a need for methods, systems and/or devices for detecting solid particles in a flowing fluid using sources such as x-rays or some other source, for example, detecting sand particles in a flowing fluid so as to provide sand analysis information.

SUMMARY OF THE INVENTION

Embodiments of the invention generally relate to detecting solid particles flowing in a fluid using sensing beams such as x-rays or optical light beams. In particular, detecting sand particles so as to provide for analysis of the sand flowing within a medium (e.g., pipe, conduit, well bore, borehole, or the like). The sand analysis may include: counting a number of sand particles that pass through a pre-determined area of a cross-section of an enclosed conduit like enclosure, e.g., conduit, tube, bore hole, well bore, or the like; determining sand grain size; sand grain size distribution; sand grain size uniformity; sand velocity; sand zoning; and sand population and distribution. Another application of the present invention is detection of gas bubbles in a flowing fluid within a medium (e.g., pipe, conduit, well bore, borehole, or the like).

According to at least one embodiment of the invention, an analyzing device for detecting particles in a fluid within a medium, the analyzing device comprising: a source adapted to transmit signals into the medium; at least one detector adapted to detect signals transmitted from the source such that the at least one detector and the source are structured and arranged on opposite sides of the medium; a processing unit in communication with the at least one detector and adapted to produce output signals representative of one of at least one particle characteristic or one or more particle property.

According to an aspect of the invention, at least one particle characteristic can be from the group consisting of one of a particle velocity distribution, a particle size distribution, an average particle velocity, an averaging size of the particles, or a particle population. Further, at least one particle characteristic can be a sand grain characteristic, such that the sand grain characteristic is from the group consisting of one of a sand grain velocity distribution, a sand grain size distribution, an average sand grain velocity, averaging size of the sand grains, a sand grain population, or a sand production rate as a function of a draw down pressure. Further, the one or more particle property is from the group consisting of one of a particle size, a mean particle size, or particle shape. It is possible the one or more particle property can be a sanding property from the group consisting of one of a sand grain size, a sand grain mean size, or a sand grain shape. Further still, the detected particles can be one or more sand grains or gas bubbles. Also, the detected signals include a primary x-ray beam, such that the analyzing device is configured to measure one or more sand grain sizes and one or more sand grain velocities by splitting the primary x-ray beam into two and measuring the sanding signal delays between them independent of the medium orientation.

According to an aspect of the invention, the analyzing device can be capable of operating at least in an approximate temperature of at least 150° C. The analyzing device can be capable of operating in one of a downhole environment, a subterranean environment or an oil field application. The source can be an x-ray source adapted to transmit x-ray signals and the at least one detector is an x-ray detector. The source can include a voltage x-ray tube or a light source with a wavelength. The voltage x-ray tube can have an operating range approximately 20-30 kV with 1 mA target current. The at least one detector can include a NaI detector coupled to a PMT in operation with the source, such that the source can be an x-ray source or a PMT having a photo-cathode operable with an optical source wavelength. The source can include an x-ray generator operable at approximately 30 kV with 1 mA target current. The medium can be from the group consisting of one or more flow line, at least one pipe, one or more conduit, a tool device, a compartment within a device, a channel, or a wellbore.

According to an aspect of the invention, the at least one detector can be a single detector. The detected particles can be at least one particle having a size with an approximate range between 50 to 1000 microns. The fluid can be moving, stimulated, or excited. The fluid can have a fluid velocity up to approximately 100 feet per second. According to an aspect of the invention, the invention can further comprise of at least one imaging device receiving output signals adapted to depict a plurality of signal sequences representative of the particle characteristics.

According to another embodiment of the invention, an analyzing device for detecting particles in a fluid within a medium, such that one or more sampling module communicates the fluid from the medium into at least one analyzing module, the analyzing device comprising: a source adapted to transmit signals into the fluid located in the at least one analyzing module; at least one detector adapted to detect signals transmitted from the source such that the at least one detector and the source are structured and arranged on opposite sides of the fluid; at least one processing unit in communication with the at least one detector and adapted to produce a plurality of output signals representative of one of at least one particle characteristic or one or more particle property.

According to an aspect of the invention, the one or more sampling module can include a channel, an intake device or a fluid intake channel or some combination thereof. The fluid intake channel can provide for evaluating one or more gravel pack. The one or more sampling module can be one of a MDT probe, a portion of the MDT probe or a device capable of operating in an oil field application so as to extract at least one sample from the fluid. The MDT probe can include at least one pumping module capable of providing for one of at least one pressure measurement or extracting at least one sample of the fluid from a borehole wall. The at least one particle characteristic can be from the group consisting of one of a particle velocity distribution, a particle size distribution, an average particle velocity, a particle size uniformity, or a particle population. The at least one particle characteristic can be a sand grain characteristic, such that the sand grain characteristic is from the group consisting of one of a sand grain velocity distribution, a sand grain size distribution, an average sand grain velocity, averaging size of the sand grains, a sand grain size uniformity, a sand grain population, or a sand production rate as a function of a draw down pressure.

According to an aspect of the invention, the detected particles can include at least one a sand grain. The one or more particle property can be from the group consisting of one of a particle size, a mean particle size, or particle shape. The one or more particle property can be a sanding property from the group consisting of one of a sand grain size, a sand grain mean size, or a sand grain shape. The detected signals may include a primary x-ray beam, such that the analyzing device is configured to measure at least one sand grain size and one or more sand grain velocities by splitting the primary x-ray beam into two and measuring the sanding signal delays between them independent of the at least one analyzing module orientation.

According to an aspect of the invention, the analyzing device can be capable of operating at least in a temperature of 150° C. The analyzing device can be capable of operating in one of a downhole environment, a subterranean environment or an oil field application. The source can be an x-ray source adapted to transmit x-ray signals and the at least one detector is an x-ray detector. The source can include a voltage x-ray tube or a light source with a wavelength. The voltage x-ray tube can have an operating range approximately 20-30 kV with 1 mA target current.

According to an aspect of the invention, the at least one detector can include one of a NaI detector coupled to a PMT in operation with the source, such that the source is an x-ray source or a PMT having a photo-cathode operable with an optical source wavelength. The source can include an x-ray generator operable at approximately 30 kV with 1 mA target current. The medium can be from the group consisting of one or more flow line, at least one pipe, one or more conduit, a tool device, a compartment within a device, a channel, or a wellbore.

According to an aspect of the invention, the invention can further comprise of at least one imaging device receiving the output signal adapted to depict a signal sequence representation of the at least one particle characteristic or the one or more particle property.

According to another embodiment of the invention, an analyzing device for detecting particles in a fluid within a medium using a plurality of signals, the analyzing device comprising: a source consisting of one of an x-ray source or an optical source adapted to transmit one of the plurality of signals into the medium; at least one detector adapted to detect signals transmitted from the source such that the at least one detector and the source are structured and arranged on opposite sides of the medium; at least one processing unit in communication with the at least one detector and adapted to produce a plurality of output signals representative of one of at least one particle characteristic or one or more particle property; and an imaging device receiving the output signals and adapted to depict at least one signal sequence representative of one of the at least one particle characteristic or the one or more particle property.

According to another embodiment of the invention, an analyzing method for detecting compositional aspects in a fluid in a medium using a plurality of signals from a source, the analyzing method comprising: a) transmitting a first signal and a second signal of the plurality of signals with the source into the fluid in the medium; b) detecting the first and the second signals transmitted through the fluid in the medium; c) recording the detected first and second signals with a processor; d) and comparing the first signal with the second signal along with an elapse time via the processor so as to provide for detection of at least one compositional aspect of the fluid.

According to an aspect of the invention, the detected compositional aspects in the fluid can include at least one particle characteristic or one or more particle property. The analyzing method can be a non-imaging technique and an imaging technique. The non-imaging technique provides for a continuous measurement for detecting individual particles. The non-imaging technique can provide for the detected signals having a primary x-ray beam, such that the analyzing method is configured to measure one or more particle sizes and one or more particle velocities by splitting the primary x-ray beam into two and measuring the particle signal delays between them independent of the medium orientation. The imaging technique can provide for a plurality of images of a section of the medium taken with an array image detector, such that each image contains two or more particles.

According to an aspect of the invention, the particle can be a sand grain. The at least one particle characteristic can be from the group consisting of one of a particle velocity distribution, a particle size distribution, an average particle velocity, an averaging size of the particles, or a particle population. The one or more particle property can be from the group consisting of one of a particle size, a mean particle size, or particle shape.

Further features and advantages of the invention will become more readily apparent from the following detailed description when taken in conjunction with the accompanying Drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 30 illustrates another routine that may be used in implementing at least one embodiment of a method of the invention.

DETAILED DESCRIPTION OF THE PREFERRED EMBODIMENTS

Figure 1:
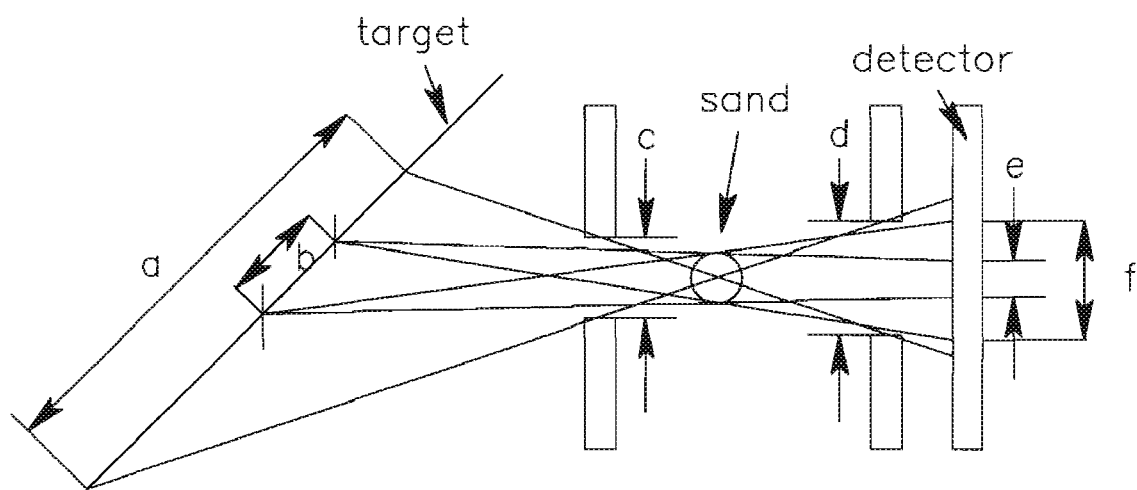
FIG. 1, illustrates a basic sand detection concept according to an embodiment of the invention.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice. Further, like reference numbers and designations in the various drawings indicated like elements.

The present invention is directed to an analyzing device for detecting particles in a fluid within a medium. The analyzing device includes: a source adapted to transmit signals into the medium; at least one detector adapted to detect signals transmitted from the source such that the at least one detector and the source are structured and arranged on opposite sides of the medium; a processing unit in communication with the at least one detector and adapted to produce at least one output signal representative of one of at least one particle characteristic or one or more particle property; and optionally an imaging device receiving the output signals which is adapted to depict at least one signal sequence representative of the at least one particle characteristic or the one or more particle property.

According to embodiments of the invention, analysis methods and/or devices used by non-intrusive or intrusive methods (e.g., x-ray analysis is non-intrusive; an advantage over intrusive method because it doesn't impede the fluid flow) and can be used to provide a visual image of a fluid in a medium used in a oil field application, e.g., production and exploration operations. For example, at least one embodiment of the invention employs a non-imaging technique using components capable of operating within a downhole environment or other oil field related environments. The analysis methods and/or devices may provide information in real-time or near real-time so that the information is used to better manage production and exploration operations. At least one advantage of using the analysis methods and devices can be the ability to improve the management of oil field applications. Further, the analysis device is capable of operating in oil field applications and can reduce the overall maintenance of the oil field equipment during production and exploration operations. Another possible advantage for using the analysis method and/or devices may include reduced costs, reduced sizing as well as simpler design and/or methods (e.g., over existing known methods and/or devices).

According to embodiments of the invention, it is noted that analysis methods and devices may be used for measuring the presence and even amounts of various other components in fluids flowing in a medium, e.g., flow line, conduit, tube, oil application channel (e.g., pipeline, wellbore, borehole, or the like). In particular, the analysis method and/or device can be used to identify and quantify the presence of water or any other components found in a mixed phase fluid or multiphase fluid (e.g., comprising of multiple components within the fluid). Additionally, an x-ray analysis method and/or device according to embodiments of the invention can be used to identify and quantify the presence of gases, metals and other components so as to provide information useful in managing infrastructure, flow and other oil related applications. However, the analysis method and/or device according to embodiments of the invention is not restricted to oil field applications but could also be used in other industries such as pharmaceutical, medical, biomedical, homeland security, military, manufacturing, or any industry that can utilize at least one advantage of an x-ray analysis method and/or device as disclosed herewith. It is possible the analysis method and/or device according to embodiments of the invention may be used to obtain fluid property or particle characteristics in the fluid which could be correlated to previously recorded compositional characteristics of the fluid. Further still, the source for producing the signals may include any suitable x-ray source capable of transmitting x-rays in desired ranges or any optical source capable of transmitting optical output signals.

Other sensing devices may be used with the method and or device so as to detect the presence of transmitted x-rays and/or the intensities of detected x-rays. Also, it is noted that x-ray intensity ranges and the intensity patterns may vary depending on the density of the fluid and/or the presence of particles in the fluid(s).

According to embodiments of the invention, methods and/or analysis devices may include some hardware components consisting of a low voltage (20-30 kV) x-ray tube and a thin (1 mm) NaI scintillator coupled to a photo-multiplier tube, or the like. The signal may be processed to remove unwanted noise and increase signal-to-noise (S/N) ratio using various algorithms and methods used in the art before being received by the processing unit. The processing unit may be a computer processor of the kind known in the art. Preferably, the processing unit can be a computer adapted to produce output signals representative of at least one particle characteristic or one or more particle property. Where in the particle characteristic may include, by non-limiting example: particle velocity distribution, particle size distribution, average particle velocity, an averaging size of the particles, or a particle population. The particle properties may include, by non-limiting example: a particle size, a mean particle size, or particle shape. However, the processing unit can simply provide a rendering of the signal information for correlating by other processors. It is possible the processing unit can receive signals from a detector and convert the signals into a signal sequence representative of the particle characteristics or particle properties. It is conceivable that other intervening devices could be arranged between the detector and the processing unit. For example, the signal may be encrypted, converted from analog to digital, compressed, or otherwise manipulated. The processing unit may be one or more devices that comprise of the processing unit. According to aspects of the invention, some components of the analysis device may be located remotely from other components.

According to embodiments of the invention, it is possible for the processor to incorporate known or predetermined behavioral characteristics, wherein the processed information can be correlated with identifiable characteristics of the detected particles such as sand or other desired particle properties/characteristics. Preferably, the information can be correlated to indicate one of: a) the amount of such particles present, e.g., sand particles; b) location of particle zones, e.g., sanding zones; c) particle production rate (sand production rate) as a function of the draw down pressure; d) mean particle size, e.g., sand grain size; and e) particle size uniformity, e.g., sand grain size uniformity. Further, sand grains may be detected as they pass through the x-ray beam, such that the response shapes may vary with the grain sizes and velocities of the sand particles. One advantage for determining particle size description according to an aspect of the invention may be for predicting pipe erosion and efficiency of well head desanders.

It is noted that according to an embodiment of the invention the analysis device will not require any in-situ calibration as opposed to known techniques which require a slurry injector to inject a known amount of sand in the stream at different flow velocities. Further still, an aspect of the invention may include a method or design that includes a configuration to measure grain sizes and velocities by splitting the primary x-ray beam into two and measuring the sanding signal delays between them. Further, it is possible with the above configuration such a method or design system would not only detect sand particles but also determine the sand population, the sand velocity, and/or the sand grain size distribution. It is noted that although an x-ray source and detector can be used in the above method and/or design to demonstrate the measurement concept, it is conceivable that an appropriate optical source and detector may also be used.

According to embodiments of the invention, the analysis device can be used without disrupting operation of oil field operations, e.g., production or exploration, as well as fluid flow. Further, it is also possible the analysis device can be used in both high pressure or low temperature environments such as subsea environments, subterranean environments and oil field application environments. The analysis device may be used on fluid samples having known amounts of the particles of interest. Wherein the analysis device is operable on moving fluid, stimulated fluid, settling fluid or excited fluid,/ what are stimulated, settling and excited fluids?/ so as to identify the behavior of the signals as well as a signal sequence representation of the particle profile. According to embodiment of the invention, at least one detector may incorporate any detection capable of detecting the relative intensity of the x-rays as a function of spatial position. Further, the detector may be capable of detecting the relative intensity of the x-rays as a function of time as well as space.

Overview of Sanding Information

A system designed solely for sanding applications can be simple and still offer valuable information. In addition, sanding information may be used to correct the measured average fluid density, which may be adversely affected by the presence of sands or clays in the fluid. Because of the enormous cost and consequences associated with various productions, completion, and/or sand treatment strategies, field operators often want to have as much information as possible to help them make the sound oil field application decisions. Among some of those include: 1) locations of the sanding zones; 2) sand production rates as a function of the draw down pressure; 3) mean grain size; and 4) grain size uniformity.

According to an aspect of the invention, an advantage over the prior art is the ability to detect very low sand population (unique to x-ray sensing beam technique) which can be important to detecting the onset of sanding. As noted above, the prior art sonic techniques generally detect the presence of sand particles, but not other attributes, e.g., grain sizes, velocities, etc., all of which, among other things, are important to assess the potential erosion to oil field applications including pipes and/or equipment. Further, sonic techniques are also not sensitive, if at all, when the sand population is low.

Figure 2:
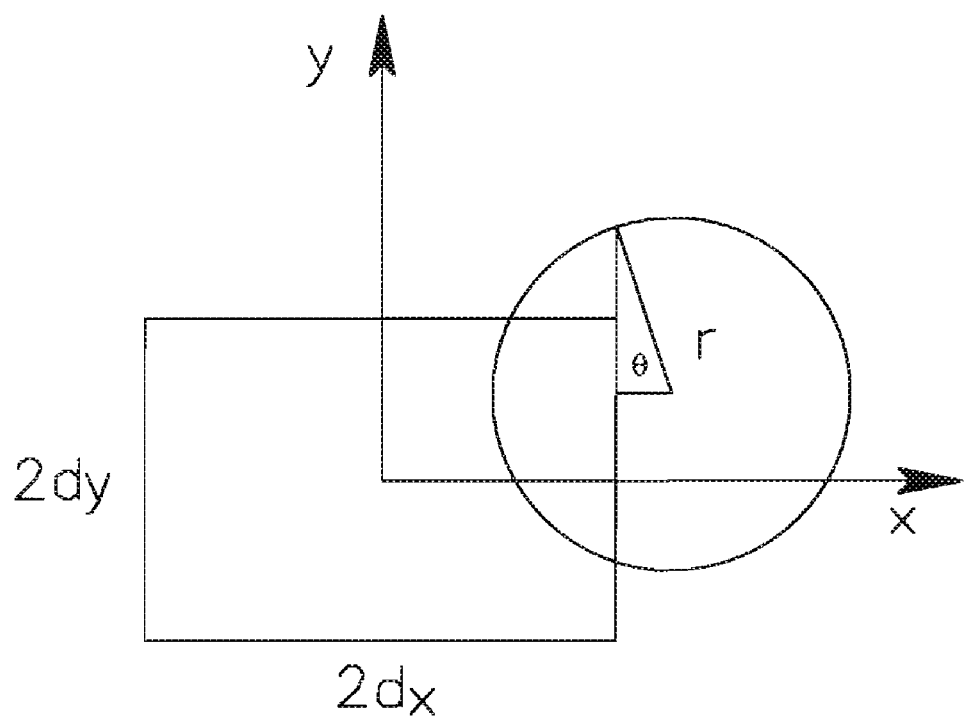
FIG. 2 illustrates a simple geometrical model of the blocking time of a spherical sand grain of radius r traversing a sensing beam with a $2d_x \times 2d_y$ cross-section according to an aspect of the invention.

FIGS. 1 and 2 illustrates methods of detection, among other things. In particular, FIG. 1 illustrates the basic measurement concept according to at least one embodiment of the invention. The analysis device/apparatus consists of an x-ray generator, a flow line, a set of x-ray beam collimators, and a detector. Also included with the apparatus is a target area viewable by the detector, the target beam spot, the source collimator, the detector collimator, the total eclipse area, and the partial eclipse area. The x-ray beam illuminates a portion of a fluid and some of the photons pass through the flow line and score hits in the detector. If the number of the scoring photons within the resolution time of the detector is sufficiently large to sample the entire Bremsstrahlung spectrum, then the measured signal, in the absence of any sand, appears as a constant DC level proportional to the amount of the energy deposited in the detector. Then a $I_0$ is used to designate the scoring photon flux density that gives rise to the DC level. The scoring photon flux is a function of the source intensity, the path length in the fluid, the attenuation power of the fluid, the size of the target beam spot b, and the sizes of the collimator openings c and d. The x-ray beam illuminates a detector area A comparable in size to the area of the detector collimator opening. For an x-ray beam spanning a very small angle, $I_0$ is approximately constant over the beam cross-section and the total number of scoring photons is $A \times I_0$. Super-imposed on this DC level are high frequency electronic and photon statistical noises. The noise amplitude is proportional to $\sqrt{A \times I_0}$ if the photon statistics dominates, which is normally the case. Because a sand particle has a much higher x-ray attenuation power than either water or oil of the same volume, a momentary drop in the otherwise constant DC level manifests its passage through the x-ray beam. During its passage the sand particle casts a shadow moving across the detector. The shadow consists of a total eclipsed region (e) and a halo, or partial eclipse region, (f−e). Then a $A_s$ is used to represent the sand shadow within A, which consists of two parts with different x-ray fluxes. We use $I_{se}$ and $A_{se}$ to designate the x-ray flux density at the detector within, and the area of, the total eclipse region. Similarly, an $1_{sf}$ and $A_{sf}$ is used to designate the same quantities in the partial eclipsed region. The reduction in the x-ray signal, or the amplitude of the sanding signal S (measured from the DC level) is therefore:

$$S = A_{se}(t)I_0 + A_{sf}(t)I_0 - A_{se}(t)I_{se} - A_{sf}(t)I_{sf} = A_{se}I_0(1-\alpha) + A_{sf}I_0(1-\beta), \quad (1)$$

where:

$I_{se} = \alpha I_0$, $I_{sf} = \beta I_0$.

Thus, we explicitly express the shadow areas as a function of time to indicate that we are dealing with a moving shadow. Both $\alpha$, $\beta$ are $\leq 1$, and $\alpha$ is the sand particle attenuation factor in the total eclipsed region whereas $\beta$ represents the average attenuation in the partial eclipsed region. The signal to noise ratio is therefore, $$S/N \approx \frac{A_{se}(1-\alpha) + A_{sf}(1-\beta)}{\sqrt{A}} \times \sqrt{I_0}. \quad (2)$$

The objective is to maximize both S and S/N. Several conclusions may be drawn from the simple geometrical model shown in FIG. 1 and eqn. (1) and (2):

a. Both S and S/N increase with $I_0$, which increases with increasing source intensity and decreasing attenuation path length in the fluid.

b. Larger sands cast larger shadows (larger $A_{se}$, $A_{sf}$) and attenuate more photons (smaller α, β) than smaller ones. Therefore both S and S/N increase with the grain size.

c. For a given grain size, S/N increases with decreasing A (note $A \geq A_{se} + A_{sf}$). The sanding signal S is the largest if the entire shadow is within A when the sand is at the center of the beam ($A = A_{se} + A_{sf}$).

e. Attenuation in the total eclipsed region is stronger than in the partial eclipsed region. The relative areas between the two are functions of the beam spot on the target. The smaller the beam spot is, the larger the central shadow area becomes. For a point source f≈e.

f. The size of the central shadow e decreases with the source to sand distance if the beam spot is smaller than the grain size and increases otherwise, whereas f always decreases with the source to sand distance. In practice, the location of the sand particle is not an issue for two reasons: (a) the path length through the flow line is usually much shorter than either the source to the flow line or the flow line to the detector distance, and (b) the sand location has little effect provided that the x-ray beam has a constant cross section comparable to the smallest sand grain. A constant x-ray beam cross section also leads to the optimal sanding sensitivity, which will be explained below.

Apart from the sizes of the sand grains over which we have no control, those conclusions clearly point to five factors that lead to large S and S/N:

1. An intense x-ray source.
2. A small electron beam spot (b in FIG. 1).
3. A short attenuation path length through the fluid.
4. A detector collimator opening greater than the total shadow area of the sand.
5. An x-ray beam cross section such that $A > \approx A_{se} + A_{sf}$.

Part of the objective of this investigation is to evaluate those desirable factors within the context of practical considerations and within the constraints of the MDT environment.

Factors (a) and (b) relate to the x-ray tube design. There are two ways to increase the source intensity: increase the high voltage or increase the beam current. However, for practical considerations (size, cost and reliability) it is desirable to operate the x-ray tube at the lowest voltage possible. Our data suggest that an x-ray tube operating between 20-30 kV with 1 mA of beam current is sufficient for our purposes. At such low voltages the combined footprint of the x-ray tube and its power supply can be quite small, perhaps not larger than 2" diameter and 10" long.

For an x-ray beam un-restricted by collimators, a MCNP simulation[1] suggests a rapid loss of the sanding signal amplitude and contrast with increasing beam spot size beyond the sand grain size. This is mainly because the central shadow e reduces, whereas the halo f increases, with the beam spot size. On the other hand, the improvement gained with a beam spot size smaller than the grain size is not significant. Since an x-ray tube with a smaller beam spot costs more, there is no incentive to make the beam spot smaller than the size of the smallest grain we care to measure, or about 50 μm. X-ray tubes meeting this beam spot specification are readily available commercially at a very low cost.

Factor (c) concerns the flow line design. The x-ray sanding analysis will benefit from a flat cell design, e.g. a 2 mm by 9 mm cell used in OFA, instead of the standard 5 mm diameter flow line. An x-ray beam passing through 2 mm of liquid gives rise to better S and S/N than one that passes through 5 mm of liquid.

The last two factors, (d) and (e), dictate aspects of the x-ray beam design. Because the low energy x-ray photons cannot penetrate the pressure containment wall of the flow line, there will always be small x-ray entrance and exit windows that also serve as the source and detector collimators. The least restrictive pair of these three parameters defines the x-ray beam cross-section: the target beam spot size (b), the source collimator opening (c) and the detector collimator opening (d). Since both the total shadow area and the shadow area within A, $A_s = A_{se} + A_{sf}$, increase with the grain size, factors (d) and (e) suggest that the detector collimator, which is the primary parameter determining the size of A, should be comparable to, but slightly larger than, the size of the smallest grain of interest. The condition $A \approx > A_s$ dictates that the detector collimator is one of the limiting parameters. The other criterion that $A \times I_0$ should be as large as possible implies that the source collimator should not be a limiting parameter. Thus, an ideal x-ray beam is defined by the beam spot size on the target and the detector collimator. The source collimator merely prevents those photons that are not on a straight line from the target to the detector from entering the flow line, and hence reduces the background due to multiple scattering events. Since we have already determined that the optimal target beam spot size should be comparable to the smallest grain size of interest, which is also comparable to A, an ideal x-ray beam has a constant cross section comparable in size to the smallest grain size we wish to measure. However, it is important to point out that the condition $A > \approx A_{se} + A_{sf}$ is meant to maximize S/N. It bears no consequence on the absolute sanding signal strength S. Since the statistical noise can be reduced significantly with the use of a properly designed high frequency filter, the size (and shape) of the detector collimator opening should only be a minor consideration. Other requirements on the beam cross section, such as those dictated by the grain size and velocity measurements to be discussed later, should take precedence.

Referring to FIG. 2, the sanding responses of such a detection system can be classified based on the grain sizes. For example, FIG. 2 shows a simple geometrical model of the blocking time of a spherical sand grain of radius r traversing an x-ray beam with a $2d_x \times 2d_y$ cross-section. To facilitate the discussion, let's assume the sand particles travel at a typical MDT flow velocity of 1 m/s, and the x-ray beam has a 200 μm×200 μm cross section. For a round 200 μm sand particle entering the central portion of the x-ray beam, the sanding signal first increases (the detected x-ray signal reduces), reaches its peak and then decreases back to the DC level. The response should have a bell or triangular shape with a base width comparable to the blocking time, or 400 μs in this case at a velocity of 1 m/s. It is noted that the blocking time is defined as the elapse time from the moment the leading edge of the particle enters the beam to the moment it is completely out of the beam. For a particle passing through the center of the beam, the blocking time is the transient time for the particle to cover a distance equal to the sum of the diameter of the beam cross section and the diameter of the particle. The amplitude is smaller if a portion of the particle falls outside of the beam. The response of a 400 μm sand particle traveling through the central portion of the x-ray beam generally has a flat top and larger amplitude than a 200 µm sand particle. The base width of the response, or the blocking time, should be about 600 µs at 1 m/s. Thus, if we know the sand velocity we can also deduce a rough estimate of the grain size from the shape and width of the sanding responses.

The relationship between the grain size and the blocking time may be derived based on a very simple geometrical model, shown in FIG. 2. Since we are interested only in the approximate dimension, rather than the exact shape, of the sand grain, we will approximate the sand grain with a sphere of radius r. It travels along the y-axis at a velocity v. In the coordinate system shown in FIG. 2, the location (the center of the sphere) along the x-axis is given by:

$$x = d_x + r \times \cos\theta \quad (3)$$

Because of the symmetry of the problem, we only need to consider the region $x \geq 0$. The particle may be detected only if $x < d_x + r$. For $x \leq d_x$, the blocking time $\tau$ is a constant, $$\tau = \frac{2d_y + 2r}{v}, \, x \leq d_x. \quad (4)$$

For $x > d_x$, the blocking time is, $$\tau = \frac{2d_y + 2r \times \sin\theta}{v} \quad (5)$$
$$= \frac{2d_y + 2r \times \sqrt{1 - \cos^2\theta}}{v}$$
$$= \frac{2d_y + 2 \times \sqrt{r^2 - (x - d_x)^2}}{v}$$

$d_x + r > x > d_x.$

The mean blocking time can be calculated from eqn. (4) and eqn. (5), $$\bar{\tau} = \int_0^{d_x+r} P(x)\tau dx \quad (6)$$
$$= \frac{1}{d_x + r}\int_0^{d_x+r} \tau dx$$
$$= \frac{1}{d_x + r}\left(\int_0^{d_x} \tau dx + \int_{d_x}^{d_x+r} \tau dx\right)$$
$$= \frac{d_x}{d_x + r} \times \frac{2d_y + 2r}{v} + \frac{r}{d_x + r} \times \frac{\left(2d_y + \frac{1}{2}\pi r\right)}{v},$$

where P(x)dx is the probability of a detected sand particle passing between x and x+dx. We have assumed that P(x)=1/(d$_x$+r) is a constant. The first term in eqn. (6) corresponds to those particles that pass through the beam ($x \leq d_x$) and the second term corresponds to those that fall outside the beam but is still within the detection zone. The mean blocking time for those latter particles, $(2d_y+0.5\pi r)/v=(2d_y+1.57r)/v$, isn't very different from the mean blocking time $(2d_y+2r)/v$ of those that pass through the center of the beam. In practice, contributions from those marginal hits are smaller than suggested by eqn. (6). Because the farther a particle is from the beam, the smaller its signal becomes, signals from those near the very edge of the detection zone will be lost in the noise.

There are also ways to reduce contributions from those "marginal hits". A simple way is to make $d_x \gg r$ at the expense of S/N ratio. Another technique is to filter out the marginal hits completely with a two-beam approach to be discussed later. Setting $0.5\pi r \approx 2r$ in the second term in eqn. (6) therefore shouldn't lead to a significant error, $$\bar{\tau} = \frac{d_x}{d_x + r} \times \frac{2d_y + 2r}{v} + \frac{r}{d_x + r} \times \frac{2d_y + \frac{1}{2}\pi r}{v} \approx \frac{2d_y + 2r}{v}. \quad (7)$$

This result is the same as would have be obtained by assuming $d_x \gg r$. The spatially averaged blocking time $\bar{\tau}$ is therefore approximately linear with the particle size 2r. The average grain size <2r> can therefore be estimated from the average blocking time <$\bar{\tau}$> of all detected particles:

$$2<r> \approx <\bar{\tau}>v - 2d_y. \quad (8)$$

We can also derive the sand concentration C from the following expression:

$$C = \frac{N}{v \times (2d_x + 2r) \times l} \quad (9)$$

where N is the number of sands detected per second and l is the x-ray beam path length inside the flow line.

According to eqn. (4) and (5), the shortest blocking time is $\tau_{min}=2d_y/v$ corresponding to $r \ll d_y$ (small sands) or $x \approx d_x+r$ (grazing hits). Consequently, grain size sensitivity drops rapidly for sand grains smaller then the height of the collimator opening. Thus the height of the beam, 2d$_y$, should be comparable to the linear dimension of the smallest sand grains of interest, consistent with the conclusion derived earlier based on S/N considerations. This, however, doesn't apply to the x-dimension. In fact, it is beneficial to make d$_x$ large as long as S/N is acceptable for several reasons.

1) Because a wider beam increases the probability of intercepting sands and
2) It reduces the contributions of the second term in eqn. (6), and
3) It increases the probability of correlated hits in a two beam velocity measurements that we will discuss now.

So far we have discussed how sand particles may be detected and how the blocking time relates to the grain size. However, to get the absolute grain size and the sand population we must also know the sand velocity as it crosses the beam. The sand velocity can be measured with a simple modification to the collimator geometry shown in FIG. 1. A single set of collimators samples a very small portion of the x-rays emitted from the x-ray tube. Likewise, only a tiny area of the detector is used in a single beam configuration. By cutting one more opening in each collimator, we can send a second x-ray beam through the flow line just below the first one. This doesn't require any additional space, nor does it increase the cost, because the same x-ray source and detector are used. If the two beams are separated by 3 mm, and a sanding signal appears in the second beam 3 ms later than the signal in the first beam, then we know the sand velocity is 1 m/s. Once the sand velocity is known, the population of the sand particles and their approximate sizes can be derived from the frequency of detection, the sand velocity and the shapes of their responses.

Figure 3:
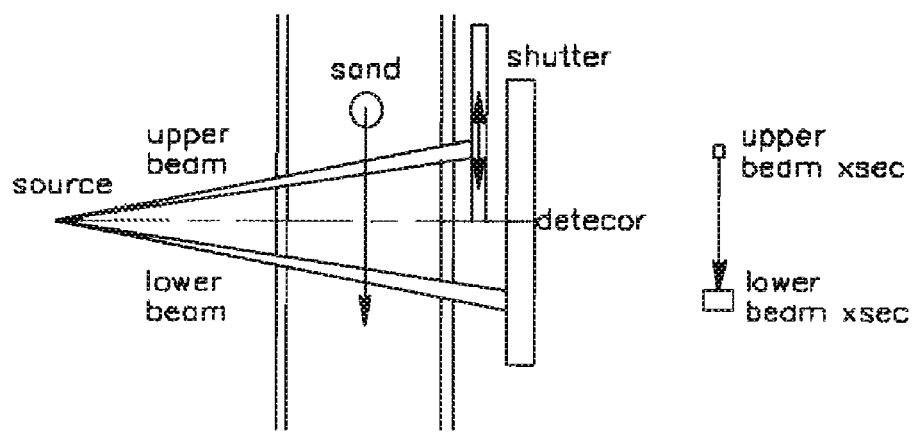
FIG. 3 illustrates a schematic diagram of a two-beam apparatus for sand velocity measurement showing a mechanical shutter and two beam paths according to an aspect of the invention.

FIG. 3 illustrates embodiments of the invention, in particular at least one apparatus illustrating a schematic diagram of a two-beam apparatus for sand velocity measurement showing a mechanical shutter and two beam paths. Our main objective is to demonstrate the basic measurement technique, specifically, its sand detection sensitivity, its ability to differentiate sand grains of different sizes, and its ability to measure the sand velocities. We used an industrial standard Oxford 5000 commercial DC x-ray source capable of delivering 1 mA of beam current at 50 kV. Its single unit cost is about $4000 including the power supply. The target beam spot size (quoted by the manufacturer) is about 70 μm. Micro-focused x-ray tubes with an electron beam target spot <10μ are also available from the same vendor and others. For downhole applications a pulsed, rather than DC x-ray generator, should be used. This is strictly a power consumption consideration and has very little to do with the system performance. The only difference between a DC and a pulsed source as far as the measurement is concerned is that a DC source has a higher average count rate.

Still referring to FIG. 3. The at least one embodiment of an apparatus shows the x-ray beam, spanning a 20° angle, exited through a side mount 250 μm thick Be window and illuminated a 6 mm (id) PEEK flow line with a wall thickness of 0.004". The distance between the flow line and the beam spot was about 1.5". Sand grains were dispensed by a vibrating hopper and dropped into the flow line through a funnel located at about 3" above the x-ray beam. We estimated that the falling velocity in air as the sand crosses the x-ray beam is about 1 m/s at a drop height of 3". A small fraction of the x-rays traversing the PEEK tube passed through the detector collimator and was detected with a 1 mm thick NaI(Tl) crystal coupled to a Hamamatsu PMT. The NaI crystal had a 125 μm Be entrance window with a low energy cutoff at about 3 keV. A typical distance between the detector collimator and the flow line was about 1". In the two-beam configuration, the upper and lower detector collimator openings were separated vertically by 5 mm. The corresponding separation between the upper and lower beams at the location of the flow line was therefore about l=3 mm. The scoring events in both beams by the same sand falling in air should therefore be separated by about 3 ms. The collimator was made from a 1/16" thick Pb sheet with either one or two precisely cut openings. We didn't use any source side collimator as shown in FIG. 1. Not using a source collimator led to a larger DC level signal because photons not on a straight path from the source to the detector could enter the flow line and score hits after scatterings in the fluid. Lack of the source collimator, however, should have little effect on the sanding signal amplitudes. The detector collimator was attached to a three-way manipulator to allow proper alignment of the collimator openings and the beam. There are two reasons why proper alignment is critical. First, the thickness of the collimator was about 1500 μm whereas the smallest opening we used was 200 μm. With this large aspect ratio, photons might not pass through the openings cleanly if the alignment was poor. Secondly, in the two-beam configuration, we didn't distinguish scoring events in the different beams. Thus it was important to make sure that a sand particle that passes through both beams in the same relative horizontal locations would register comparable signal amplitudes in the detector. The source beam spot should locate about halfway between the upper and lower detector collimator openings in a properly aligned system. Since the collimator jaws have square edges as shown in FIG. 4, a properly aligned two-beam configuration reduces the effective opening height ($2d_y$) by about 100 μm.

It is to be understood that FIG. 3 illustrates an embodiment used to demonstrate the invention. In high temperature high pressure environment of downhole applications variations of the embodiment may be used. For example, a different types of scintillator may be more advantageous; the detector compartment may be pressure compensated, and the light from the crystal is coupled to the PMT through a light pipe and a transparent high pressure window.

Figure 4:
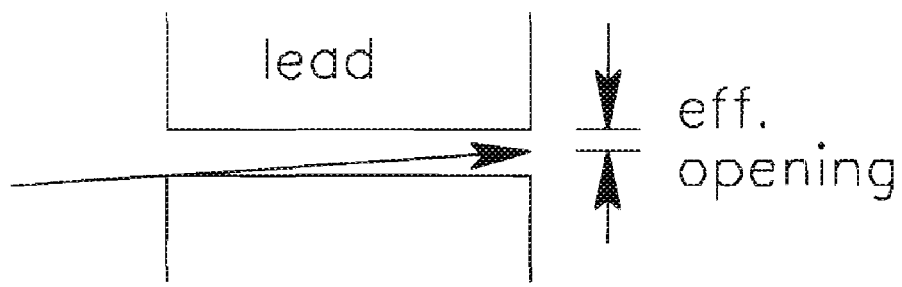
FIG. 4 illustrates a detailed geometry of the upper detector collimator jaws. The shadow cast by the lower jaw reduces the effective vertical openings by about 100 μm according to an aspect of the invention.

FIG. 4 illustrates geometry of the upper detector collimator jaws, wherein the shadow cast by the lower jaw reduces the effective vertical openings by about 100 μm.

Referring back to FIG. 3, such that FIG. 3 shows a shutter between the detector collimator and the detector. We didn't need or use the shutter for data presented in FIGS. 9-27. Nevertheless, a shutter may be incorporated as a further improvement. We include it in the figure to facilitate later discussions. As discussed further below, FIG. 5 shows pictures of the PEEK tube attached to the x-ray tube exit window and a typical detector collimator (two 0.03"×0.008" slots separated by 5 mm).

As mentioned above, if we had used a flat 2 mm×9 mm cell instead of a round tube and send the x-rays through the 2 mm dimension, the sanding signal would be significantly larger. However, instead of using a flat cell we chose to look at the 6 mm flow line arrangement for ease of implementation and as a worst case scenario. We can still estimate the improvement to be gained with a flat cell by measuring sanding signals in air.

Figure 5A:
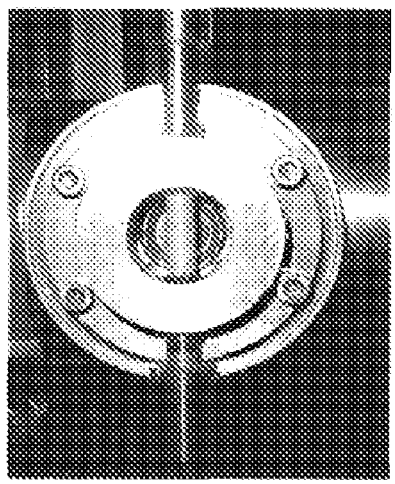
FIGS. 5a and 5b illustrate pictures of the PEEK tube attached to the x-ray window and a two-beam detector collimator (two 0.03"×0.008" slots separated by 5 mm) according to an aspect of the invention.
Figure 5B:
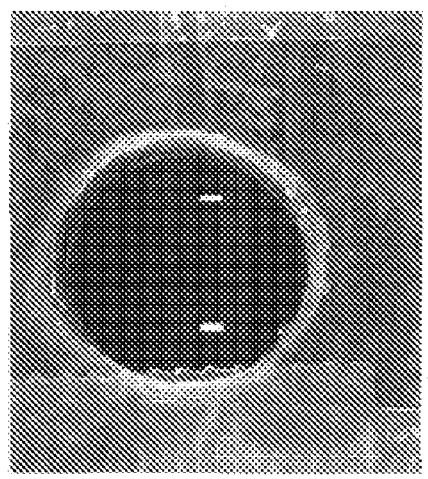

FIGS. 5*a* and 5*b* illustrate pictures of the PEEK tube attached to the x-ray window and a two-beam detector collimator (two 0.03"×0.008" slots separated by 5 mm).

Figure 6:
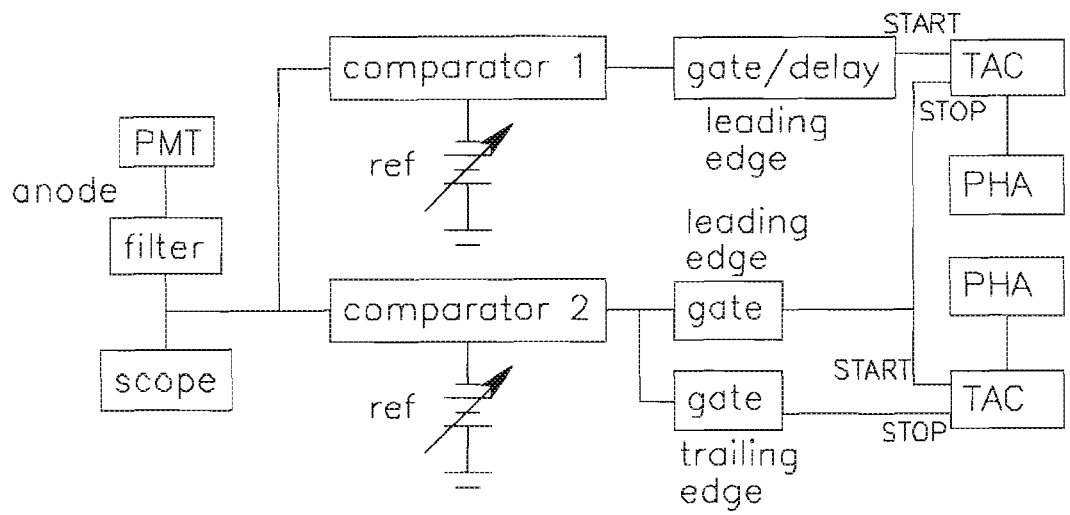
FIGS. 6 illustrate a simplified diagram of the electronics used for data acquisition according to an aspect of the invention.

FIG. 6 shows a simplified schematic diagram of the electronics used for data acquisition. The PMT (photo-multiplier tube) anode was grounded through a 10 kΩ resistor. The negative polarity anode signals were large enough to be observed directly on a scope without further amplification. We estimate the detector response time (NaI decay time plus the RC time constant due to the 10 kΩ resistor and parasitic capacitance in the system) to be <≈1 μs. The NaI/PMT combination operating in the energy deposition mode for a high photon flux behaves like a current source similar to a photo diode but with a very high gain. Using a comparable geometry, MCNP simulations[1] suggested a scoring flux of ≈40/μs in a 200μ×200μ detector area for a 60 kV, 1 mA beam with a 200μ beam spot. The attenuation path used in the simulation was 7 mm and the fluid density was 0.7 g/cc $CH_2$. The expected statistical noise was about 15% of the DC level, consistent with our experimental observations. At >1 MHz, the noise frequency is much higher than the response frequencies of the sanding signals and the noise amplitude can be reduced very effectively with a low pass filter. The cutoff frequency of a 5-pole low pass filter was carefully chosen to avoid changing the shapes of the sanding responses. Typical cutoff frequency employed was between 0.3-5 MHz depending upon S/N ratios.

Still referring to FIG. 6, the filtered signals were fed to two identical comparators. The comparator's (negative) reference voltages were normally set at just above the DC level noise. The comparator outputs were TTL level signals whose widths were equal to the widths of the input signals at the reference voltages. If a comparator's reference voltage is set near the DC level, its output signal's width is the same as the blocking times (see FIGS. 22 and 23). Outputs from comparator #1 were sent to a gate generator that triggered on the leading edge of the TTL signals and generated delayed (typically 2 ms), narrow (typically 20 μs) TTL pulses. Outputs from comparator #2 were sent to a second gate generator to generate similar timing pulses, which were not delayed. The delayed and non-delayed timing pulses were used as the START and STOP signals for the TAC (time-to-amplitude converter), respectively. The reason for delaying the START signals is because the particular TAC we used will generate an output only if a STOP signal appears within 2 ms after the START signal, which is shorter than the estimated correlation time of 3 ms for sands falling in air. The TAC outputs were fed to a PHA to produce a coincidence spectrum whose peak position corresponds to the correlation time minus the delay time of the start signals. The average sand velocity is the correlation time divided by the separation between the two beams, which was about 3 mm.

Also referring to FIG. 6, to measure the blocking time distribution we split the signals from comparator #2 and fed one of those into a third gate generator that triggered on the trailing edge of the comparator's outputs. Typical pulse widths from the two gate generators were about 20 µs and both were not delayed. The leading-edge pulses were used as the START signals whereas the trailing-edge signals were used as the STOP signals for the TAC. The outputs of the TAC were sent to a PHA to generate a comparator output width distribution. This distribution approximates the blocking time distribution if the reference voltage was set near the DC noise level.

Figure 7:
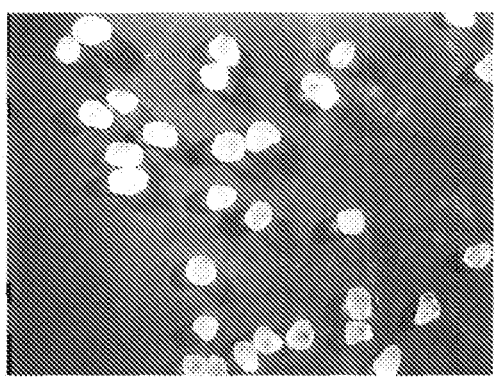
FIGS. 7 illustrates a picture of nominal 500μ sands, wherein the grain sizes vary from about 450μ to about 850μ in this frame according to an aspect of the invention.
Figure 8:
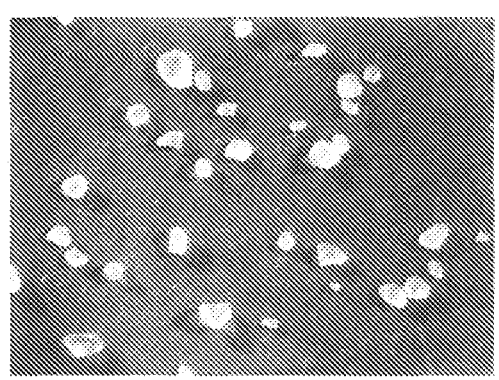
FIG. 8 illustrates a picture of nominal 150μ sands, wherein the grain sizes vary from about 50μ to about 250μ in this frame according to an aspect of the invention.

Referring to FIGS. 7 and 8, such that when looking at two different grain sizes, nominal 150 µm and 500 µm. It is noted that FIGS. 7 and 8 illustrate microscope pictures of those two different sand grains. FIG. 7 shows a picture of nominal 500µ sands. FIG. 8 shows a picture of nominal 150µ sands. The grain sizes vary from about 50µ to about 250µ in this frame The grain sizes vary from about 450µ to about 850µ in this frame We found that 500 µm sands were more uniform in size than 150 µm sands. The latter also contained many particles much smaller than 100 µm. The PEEK tube was either filled with water or air. At about 1 m/s the sand falling velocity in air as the sand crossed the x-ray beam was comparable to the MDT flow velocity. The sand falling velocity in water could not be easily estimated.

Figure 9:
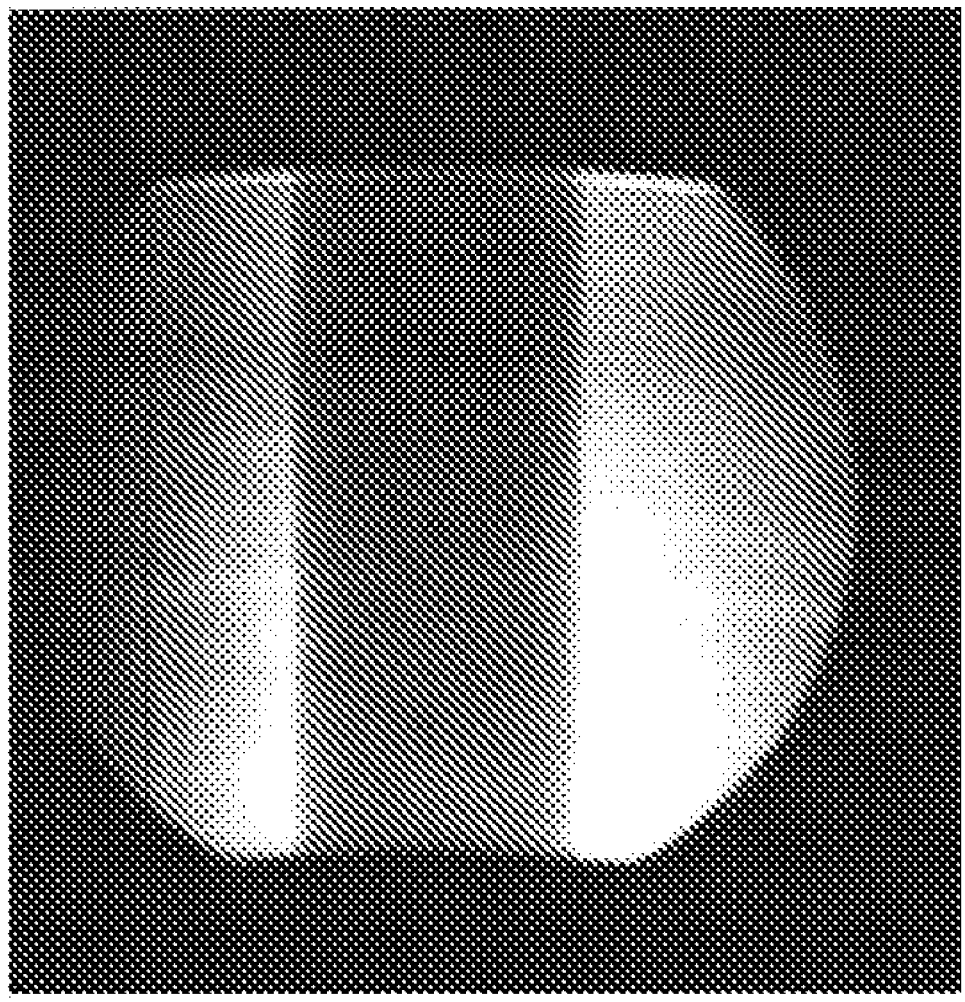
FIG. 9 illustrates a double exposure image of free falling 500μ sands in water taken with a ShadowCam 2"×2" photo sensor array according to an aspect of the invention.

FIG. 9 illustrates a double exposure image of the 500 µm sand particles falling in water taken with a 2"×2" photo sensor array, from which we estimated the velocity to be about 0.1 m/s for 500 µm sands, and slower for smaller sands. It is noted the diameter of the water filled PEEK tube was 6 mm. The exposure time was 4 ms and the two shots were taken 36ms apart. The X-ray tube operated at 30 kV and 0.8 mA. The first image of the particle at the upper left corner was outside the frame. Note that two of the particles were falling at about the same velocity (~0.1 m/sec) whereas the third one was slightly slower. The sand velocity in water in our experiment was much slower than the typical MDT flow velocity. We therefore used the water data mainly to gauge the sanding signal amplitudes, and used the air data for velocity measurements, to study the sanding responses shapes, as well as to estimate the signal amplitudes for fluid paths much shorter than 6 mm. All data presented in this report were measured at 1 mA beam current, but at various high voltages. We will first examine responses shapes from different size sands and in different media (air or water), followed by discussions on velocity and grain size distribution measurements.

Figure 10:
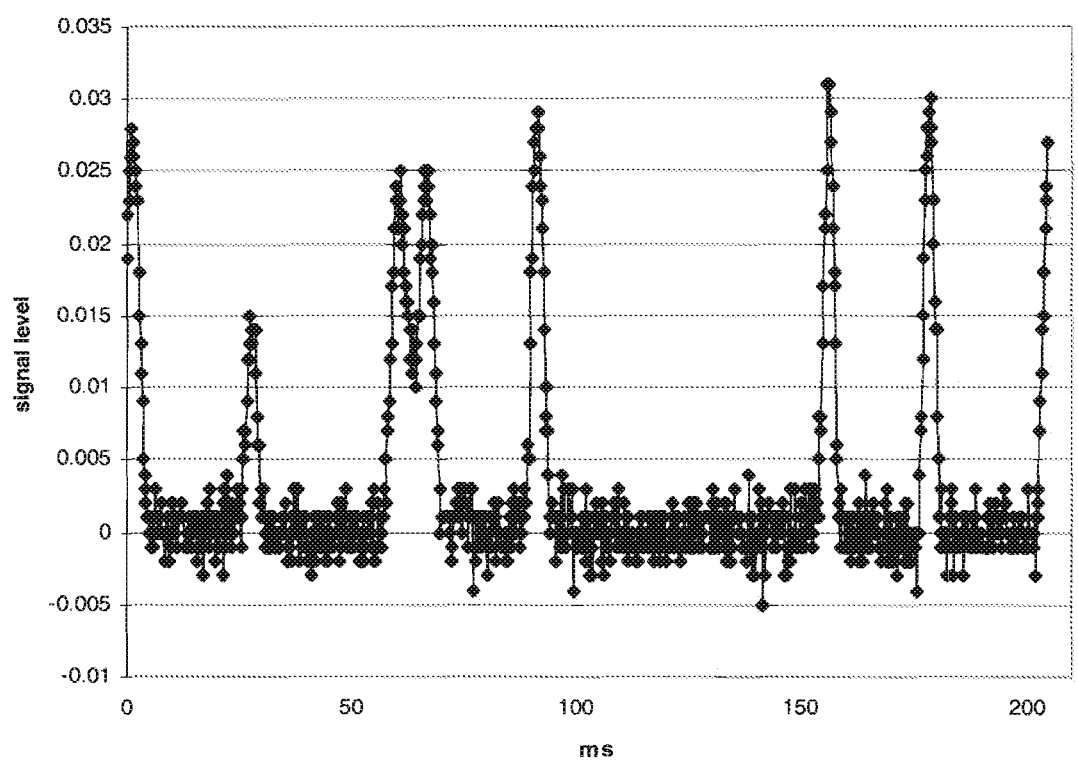
FIG. 10 illustrates sanding signals from nominal 500 μm sands free falling in water with the x-ray generator operated at 30 kV/1 mA, according to an aspect of the invention.

FIG. 10 shows a typical sanding signals sequence for nominal 500 µm sands in water. The x-ray generator was set at 30 kV and 1 mA. The detector collimator was a 1/16" thick Pb with a 400 µm diameter hole. The vertical axis is in volts and the horizontal axis is the scope time base, in ms. The PMT anode signal was first filtered through a 5-pole TCI 1982 filter box with its high frequency cutoff set at 2 MHz, then AC coupled to a Tektronics DSA 601 digital scope. Without the filter the DC level was about −70 mV with 20 mV peak-to-peak noises. With the filter, the noise is reduced to about 5 mV.

The scope was triggered with an external pulser. In this case, a total of 8 sand particles crossed the 400 µm diameter x-ray beam during a 200 ms period. According to eqn. (9) the concentration of sand particles is approximately:

$$C \approx \frac{8}{(0.4 \text{ mm} + 0.5 \text{ mm} \times 2) \times 6 \text{ mm} \times (0.1 \text{ m/s}) \times 200 \text{ ms}}$$
$$= 0.048/\text{mm}^3.$$

Figure 11:
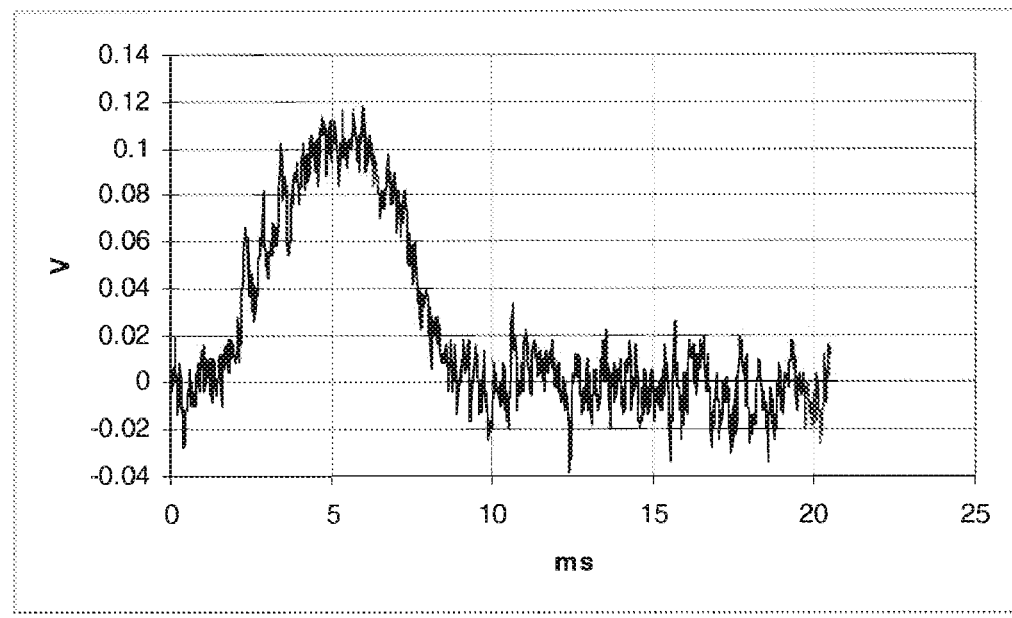
FIG. 11 illustrates sanding signal of a nominal 500μ sand particle falling through water with the x-ray tube voltage at 50 kV (run #135) according to an aspect of the invention.

FIG. 11 shows a sanding signal of a nominal 500µ sand particle falling through water. The x-ray tube voltage was at 50 kV (run #135). The vertical axis is the signal amplitude, in volts. The horizontal axis is the scope's time base, in ms.

Figure 12:
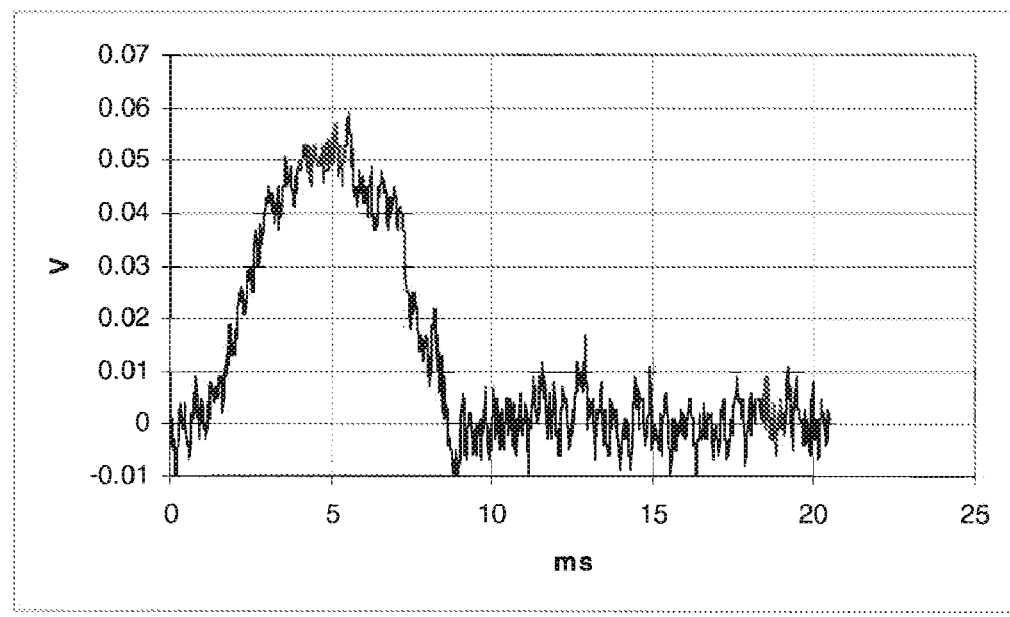
FIG. 12 illustrates sanding signals from nominal 500 μm sands free falling in water with the x-ray tube voltage at 30 kV (run #107) according to an aspect of the invention.
Figure 13:
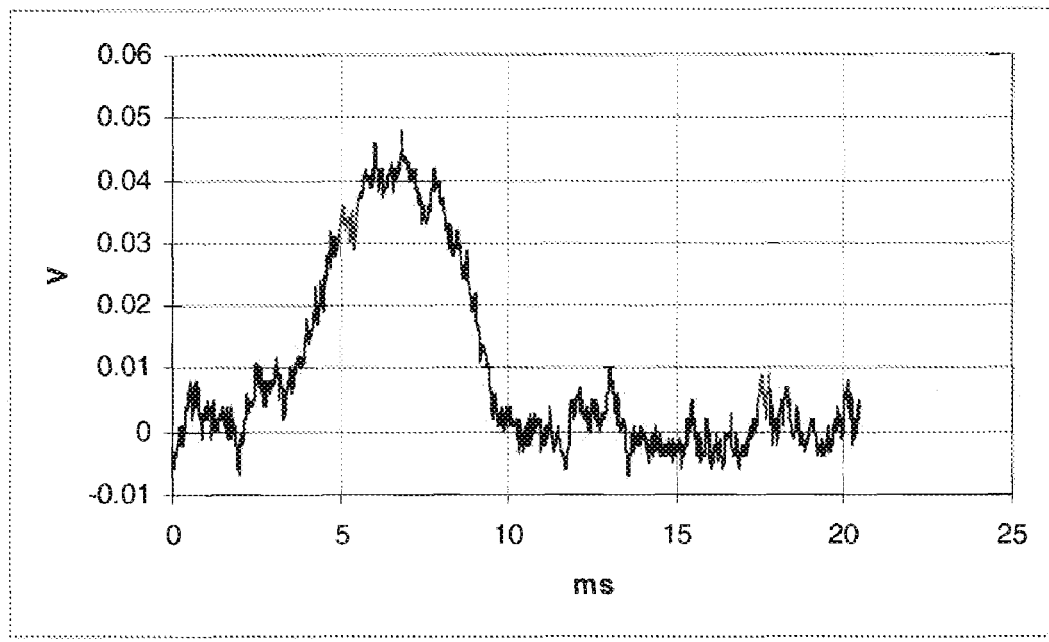
FIG. 13 illustrates sanding signal of a nominal 150μ sand particle falling through water with the x-ray tube voltage at 50 kV (run #185) according to an aspect of the invention.
Figure 14:
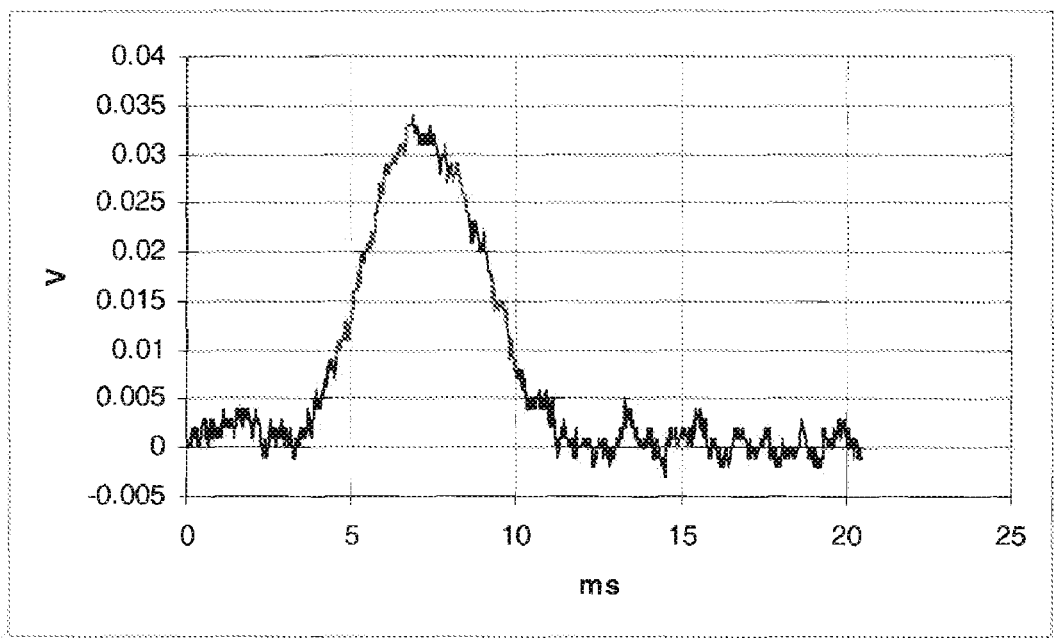
FIG. 14 illustrates sanding signal of a nominal 150μ sand particle falling through water with the x-ray tube voltage was at 30 kV (run #156) according to an aspect of the invention.

Referring to FIGS. 11 to 14, it is noted that a 400 µm diameter collimator hole is too large for smaller sand grains if we wish to obtain the grain size information. Further, FIGS. 11-14 are typical sanding signals in water for 500 µm and 150 µm sands with a 200 µm×200 µm collimator and the x-ray source was at either 30 or 50 kV. FIG. 12 shows a sanding signal of a nominal 500µ sand particle falling through water. The x-ray tube voltage was at 30 kV (run #107). FIG. 13 shows a sanding signal of a nominal 150µ sand particle falling through water. The x-ray tube voltage was at 50 kV (run #185). FIG. 14 shows a sanding signal of a nominal 150µ sand particle falling through water. The x-ray tube voltage was at 30 kV (run #156).

Figure 15:
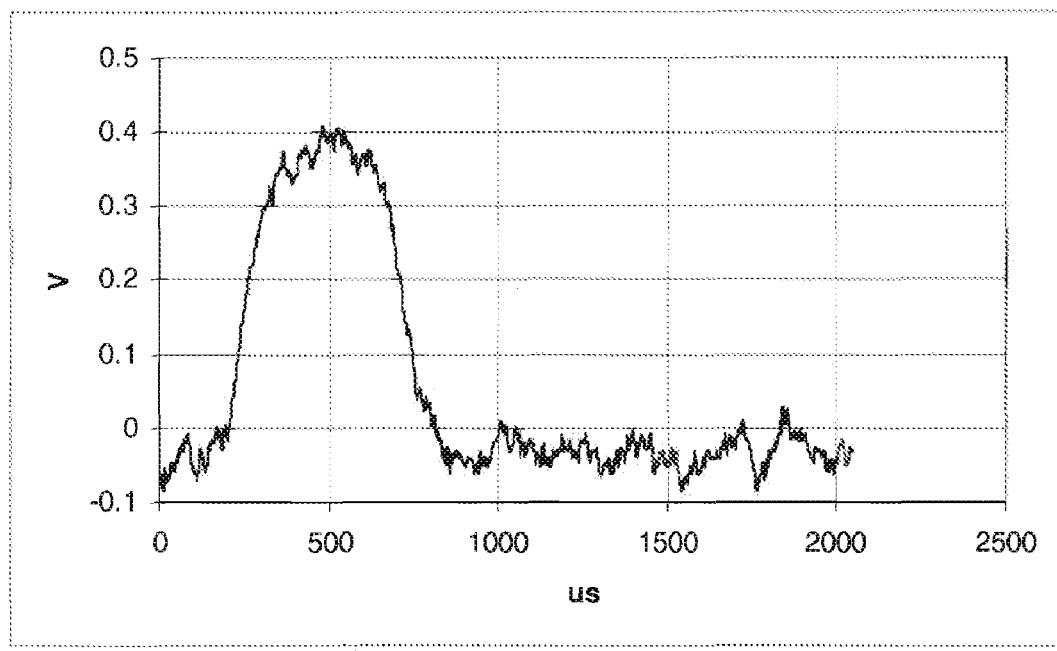
FIG. 15 illustrates sanding signal of a nominal 500μ sand particle falling through air with the x-ray tube voltage at 50 kV (run #100) and τ≈616 μs according to an aspect of the invention.
Figure 16:
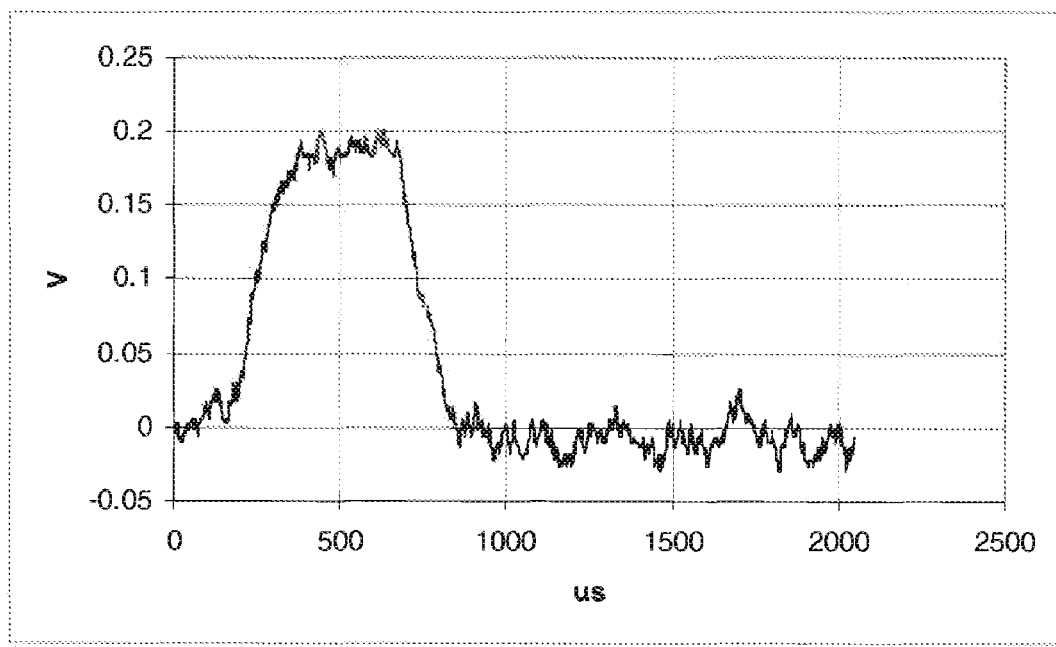
FIG. 16 illustrates sanding signal of a nominal 500μ sand particle falling through air with the x-ray tube voltage at 30 kV (run #76) and τ≈676 μs according to an aspect of the invention.
Figure 17:
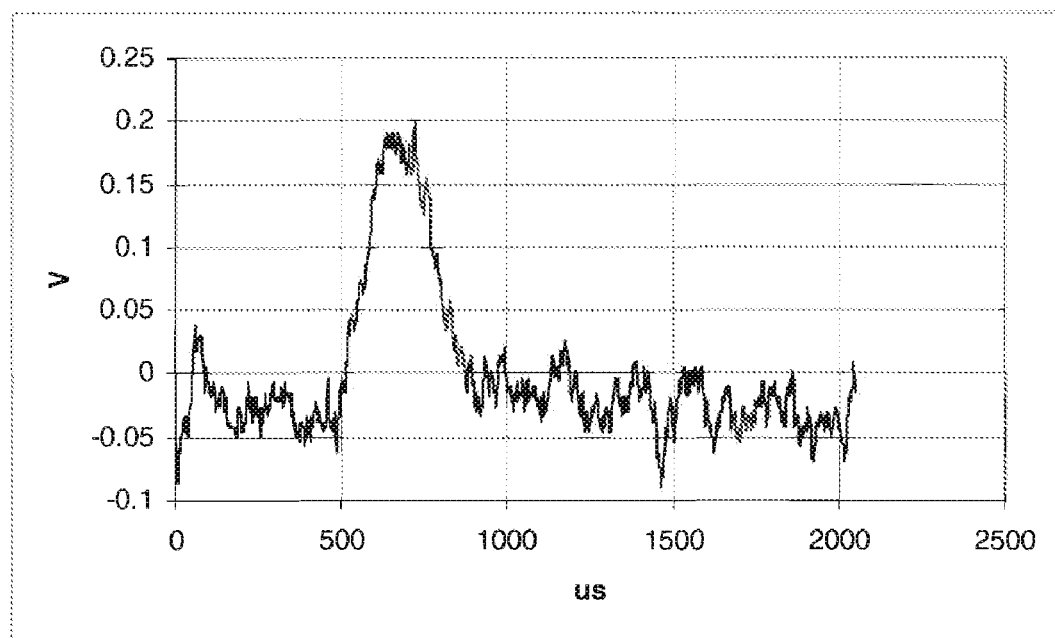
FIG. 17 illustrates sanding signal of a nominal 150μ sand particle falling through air with the x-ray tube voltage was at 50 kV (run #47) and c≈384 μs according to an aspect of the invention.
Figure 18:
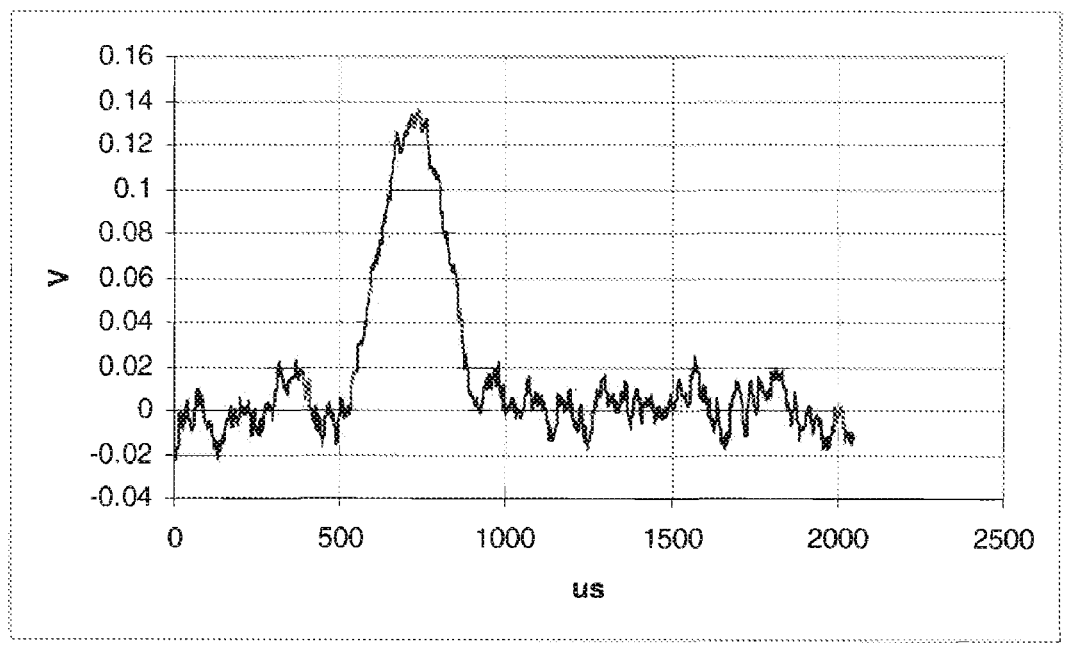
FIG. 18 illustrates sanding signal of a nominal 150μ sand particle falling through air with the x-ray tube voltage at 30 kV (run #16) and τ≈400 μs according to an aspect of the invention.

FIGS. 15-18 are similar data in air. For those data the filter cutoff frequency was set at 5 MHz for sands falling in air. For sands falling in water, the cutoff frequency was set at 2 MHz for 500 µm sands and 300 kHz for 150 µm sands, which accounts for the difference in the noise amplitudes between the two. For all those data the collimator had only one opening and was aligned with the source beam spot by maximizing the intensity. There was no reduction in the effective vertical opening. FIG. 15 shows a sanding signal of a nominal 500µ sand particle falling through air. The x-ray tube voltage was at 50 kV (run #100) and τ≈616 µs. FIG. 16 shows a sanding signal of a nominal 500µ sand particle falling through air. The x-ray tube voltage was at 30 kV (run #76) and τ≈676 µs. FIG. 17 shows a sanding signal of a nominal 150µ sand particle falling through air. The x-ray tube voltage was at 50 kV (run #47) and τ≈384µs. FIG. 18 shows a sanding signal of a nominal 150µ sand particle falling through air. The x-ray tube voltage was at 30 kV (run #16) and τ≈400 µs.

The water data clearly demonstrate the sensitivity of the technique. Even through 6 mm of water, the signals from 150 µm sands are well above the noise, suggesting that the detection threshold is probably much less than 100 µm, especially if we reduce the x-ray path in water to 1 or 2 mm. Another important conclusion we may draw is that the signal quality taken at 30 kV isn't much different from those taken at 50 kV. The reduction in noise and the increase in Pe contrast between sand and water more than compensate the lower signal levels at 30 kV. As mentioned earlier, a lower voltage source is preferred for a downhole application of this technique because it is smaller, more reliable and costs less.

The differences in the widths of the sanding responses in air and in water clearly reflect the falling velocity disparity in those two media. The differences in the widths and shapes between 150 µm and 500 µm sands falling in air are also quite striking. Assuming all particles are falling at the same velocity of 1 m/s, the estimated sizes of the four sand grains falling in air are 416µ, 476µ, 184µ and 200 µ. Note that the signal levels in air are about 4-5 times larger than in water, suggesting that a gain of at least a factor of 2 in signal strength if we reduce the water path length to 2 mm or less.

Figure 19:
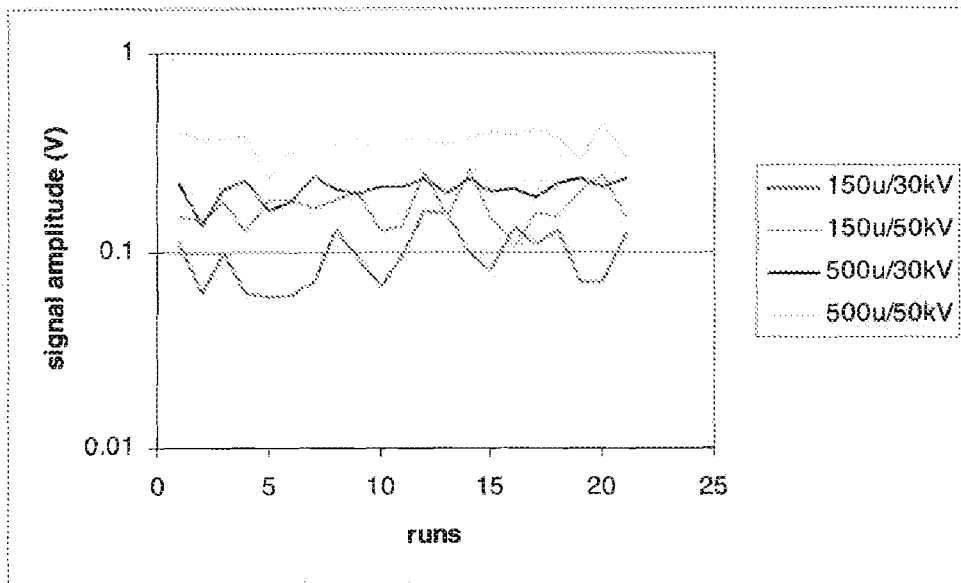
FIG. 19 illustrates peak signal amplitudes of detected sand grains falling in air according to an aspect of the invention.
Figure 20:
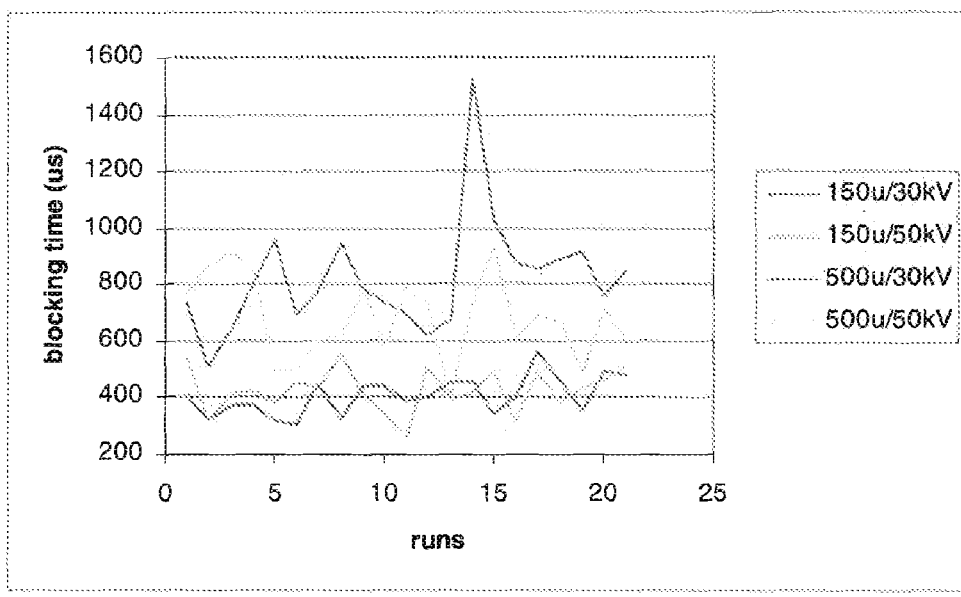
FIG. 20 illustrates blocking times of detected sand grains falling in air according to an aspect of the invention.

Referring to FIGS. 19 and 20, distributions of the peak amplitudes and blocking times for FIG. 20 detected sand grains falling in air (FIG. 19) were extracted manually and are shown in FIGS. 19 and 20, respectively. As expected, on average, the signal levels at 50 kV are higher than at 30 kV, and are higher for the nominal 500 μm sands than for 150 μm sands. Because the minimum blocking time was 200 μs (due to "grazing" hits) independent of the actual particle sizes, we expect 500μ sands to exhibit a wider blocking time variation than do the 150μ sands, consistent with the observations. The average blocking times are about 400 μs for the nominal 150 μm sands and 800 μs for the nominal 500 μm sands. Using 1 m/s as the falling velocity for both, the average grain sizes were about 200 μm for the 150 μm sands and 600 μm for the 500 μm sands. It is noted those traces were manually selected on a digital scope with the intention to illustrate the relation between the observed blocking times and the sizes of the sands. Consequently, there was a bias toward larger signals, especially for the nominal 150 μm sands. Judging from the image in FIG. 6 we suspected that the average size should be much smaller than 200 μm. This was confirmed later by unbiased data. Although those results were not too far off the sizes observed in FIGS. 7 and 8, one shouldn't take results based only on 20 events too seriously. In addition, since the horizontal dimension (200 μm) of the collimator wasn't much larger than the grain sizes, a significant numbers of the scores may be marginal hits. According to eqn. (7), when there are a large number of marginal hits, the mean grain size derived from the mean blocking time may be slightly larger than the true mean size. Making the beam wider and/or use a slightly narrower upper beam to filter out those marginal hits in the lower beam in a correlation measurement will improve the results significantly.

Figure 21:
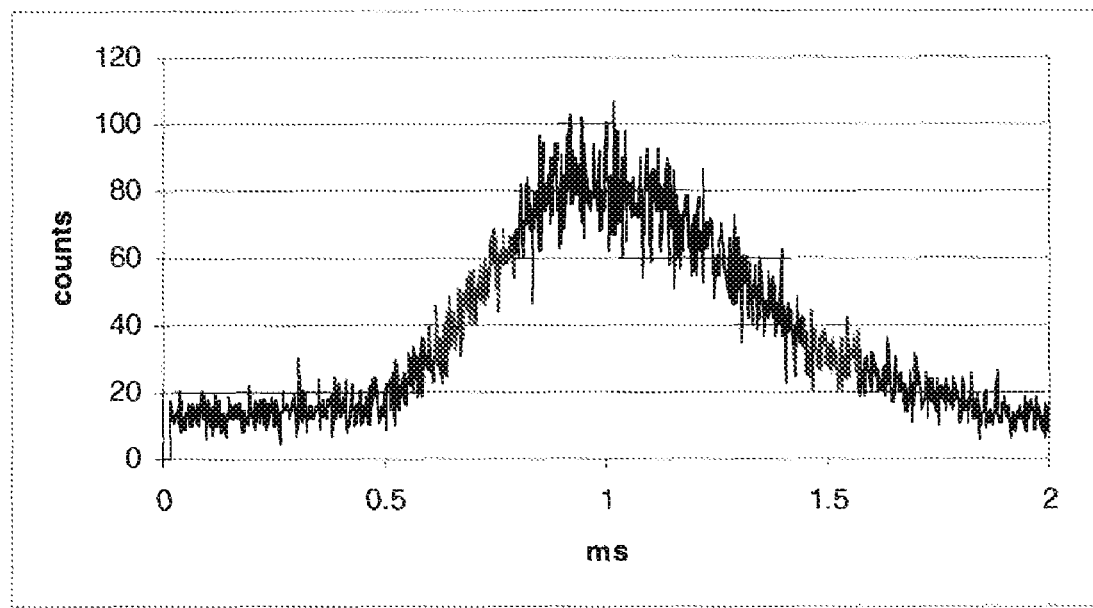
FIG. 21 illustrates a coincidence spectrum of scoring events for 500 μm sands falling in air with the TAC STARTs delayed by 2.25 ms, thus the mean correlation time being 3.25 ms according to an aspect of the invention.

FIG. 21 is a measured pair correlation function between scoring events of nominal 500 μm sands falling in air in a two-beam configuration described in the previous section. Both the upper and lower collimator openings were 3000 μm×200 μm(height). The effective 2d$_y$ was about 100 μm. The x-ray source was at 21 kV and the filter's low frequency cutoff was set at 1 MHz. The TAC spectrum covered a 2 ms duration (1024 PHA channels) and the START signal delay was 2.25 ms. Since the correlation peak was located at about 1 ms, the correlation time, or the time it takes for a sand particle to cover the 3 mm separation between the upper and lower beams was 3.25 ms, and the mean falling velocity was therefore ≈0.9 m/s. As discussed above, FIG. 21 shows a coincidence spectrum of scoring events for 500 μm sands falling in air. Further, the TAC STARTs were delayed by 2.25 ms, thus the mean correlation time was 3.25 ms.

Figure 22:
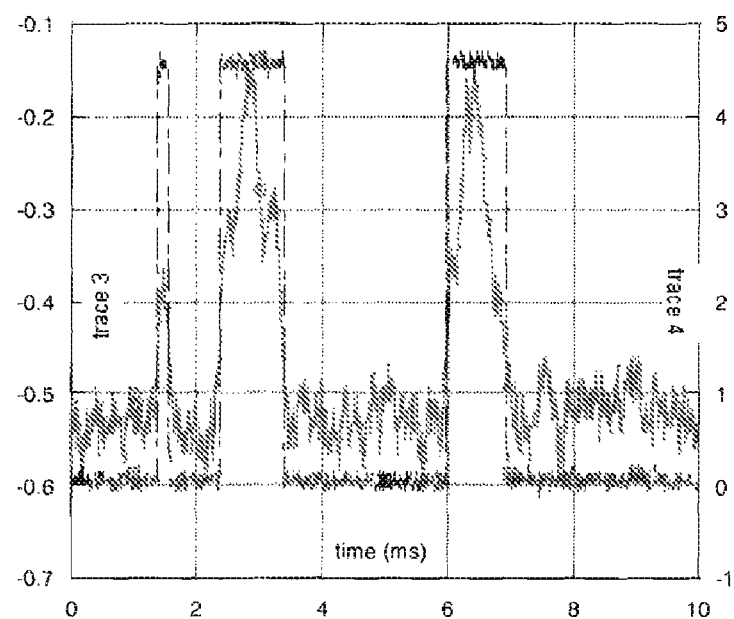
FIG. 22 illustrates scope traces of sanding signals (trace 3 in red) and the corresponding comparator outputs (trace 4 in blue) according to an aspect of the invention.
Figure 23:
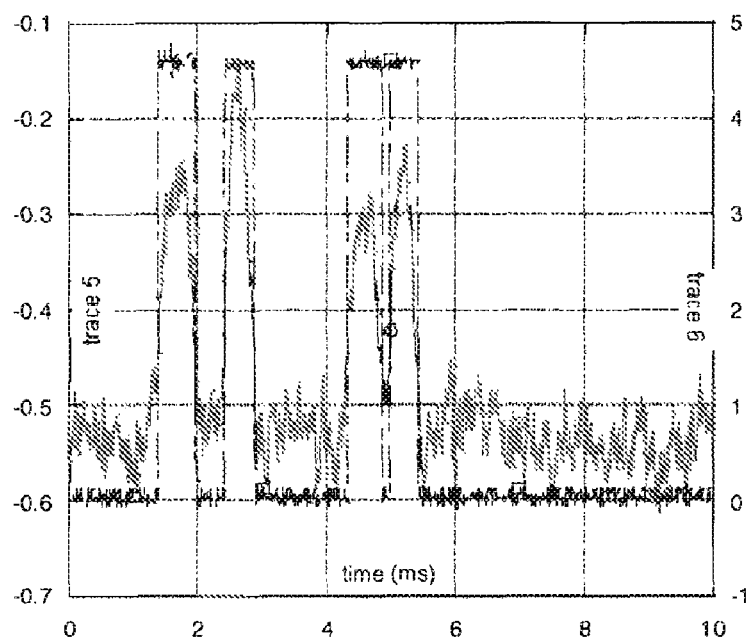
FIG. 23 illustrates scope traces of sanding signals (trace 5 in red) and the corresponding comparator outputs (trace 6 in blue) according to an aspect of the invention.

FIGS. 22 and 23 are two scope traces of sanding signals separated by roughly 3 ms. Based on the similarity in the response shapes, it's evident that those signals correspond to the upper and lower beams scores by the same sands. FIG. 22 shows the scope traces of sanding signals (trace 3 in red) and the corresponding comparator outputs (trace 4 in blue). Both vertical axes are in volts. FIG. 23 shows scope traces of sanding signals (trace 5 in red) and the corresponding comparator outputs (trace 6 in blue). Both vertical axes are in volts.

Figure 24:
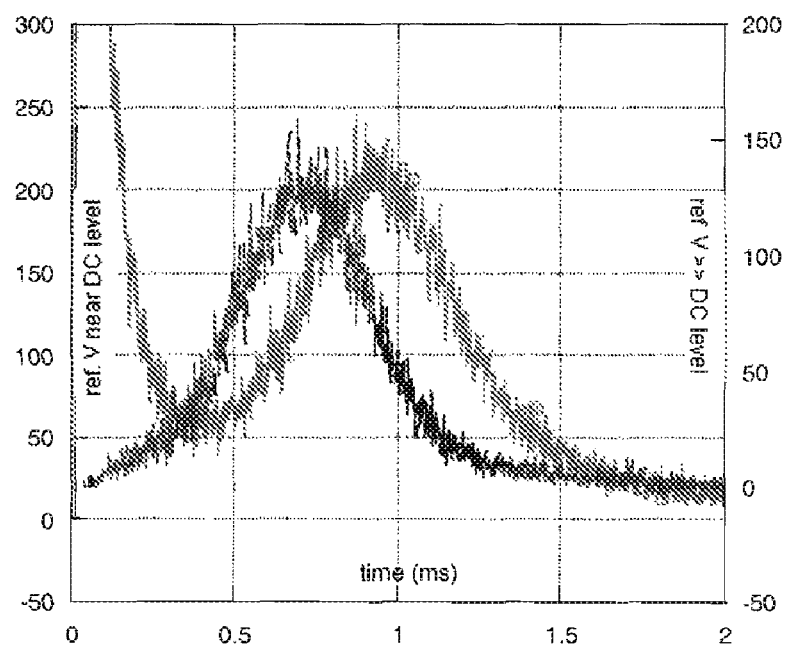
FIG. 24 illustrates a sanding signal width distributions for the nominal 500 μm sands falling in air with comparator's reference voltage set at near the DC level noise edge (red trace) or 80 mV above the DC level (blue trace) according to an aspect of the invention.

FIG. 24 shows two measured blocking time distributions for 500 μm sands using identical measurement parameters as in FIG. 21 but at two different comparator reference voltage settings; one was set at about 80 mV above the DC level whereas the other one was set at just below the noise edge. Clearly, the one set at 80 mV above the DC level under estimated the distribution because the comparator outputs widths were narrower than the base widths of the sanding signals. The most probable blocking time was about 0.9 ms; correspond to a grain size of 700 μm at an average velocity at 0.9 m/s. In part, FIG. 24 shows the sanding signal width distributions for the nominal 500 μm sands falling in air with comparator's reference voltage set at near the DC level noise edge (red trace) or 80 mV above the DC level (blue trace).

Figure 25:
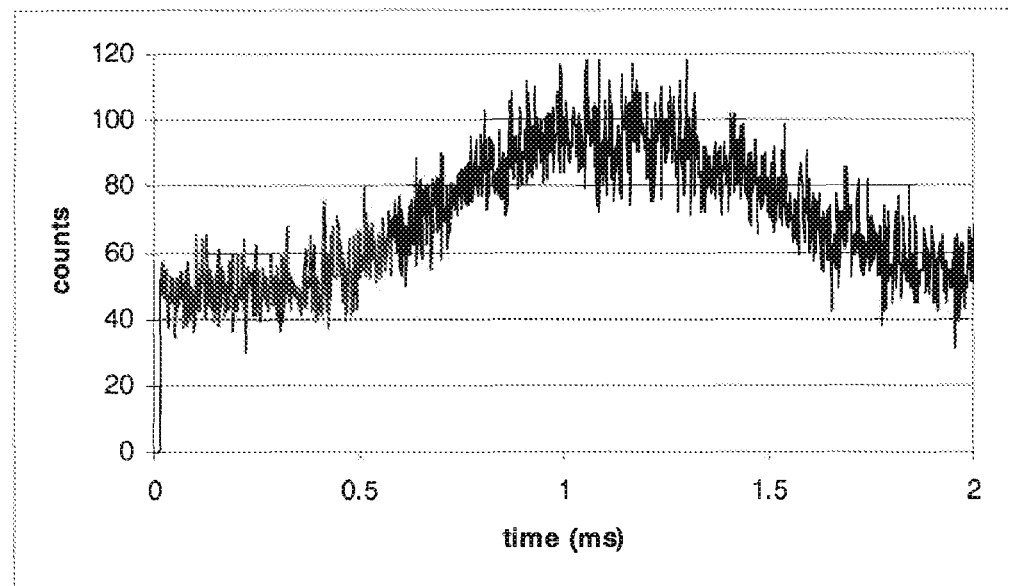
FIG. 25 illustrates a coincidence spectrum of scoring events for 150 μm sands falling in air with the TAC STARTs delayed by 2.6 ms, thus the mean correlation time being 3.7 ms according to an aspect of the invention.
Figure 26:
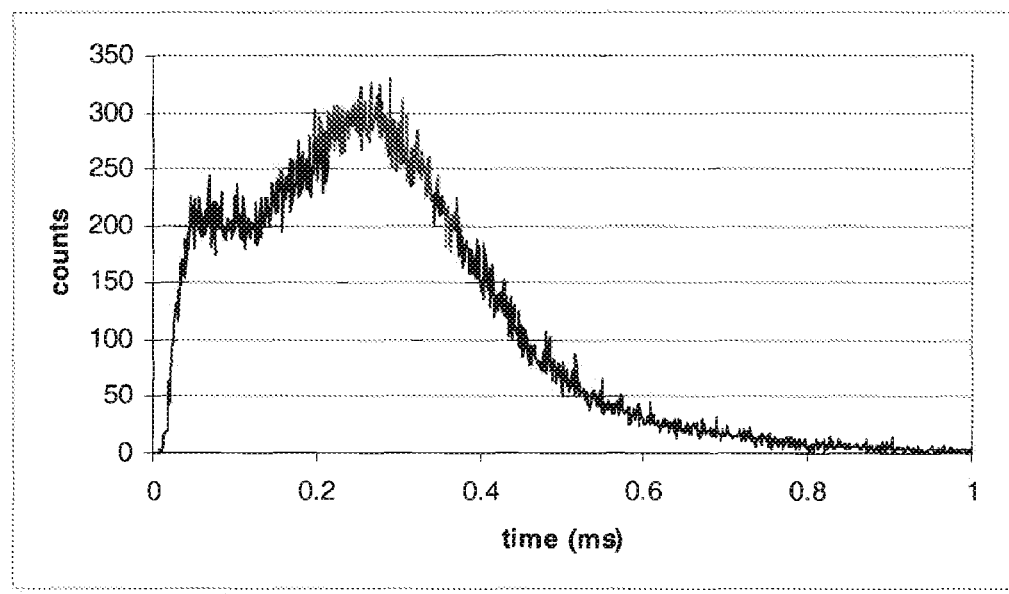
FIG. 26 illustrates a sanding signal width distribution for the nominal 150 μm sands falling in air with comparator's reference voltage set at near the DC level noise edge, such that both collimator openings were 750 μm×200 μm, respectively, and the x-ray source are at 40 kV, 1 mA according to an aspect of the invention.
Figure 27:
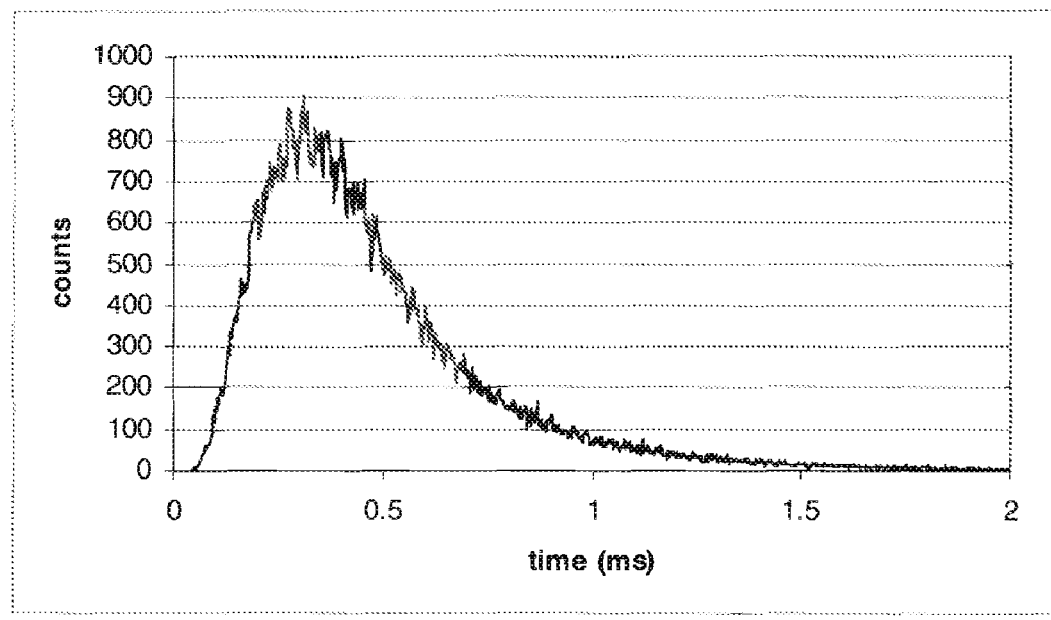
FIG. 27 illustrates a sanding signal width distributions for the nominal 150 μm sands falling in air with comparator's reference voltage set at 40 mV above the DC level, wherein both collimator openings were 3000 μm×200 μm, respectively, and the x-ray source was at 21 kV, 1 mAr according to an aspect of the invention.

Referring to FIGS. 25 to 27, FIG. 25 shows the pair correlation function for the nominal 150 μm sands falling through air. To increase the S/N ratio both the upper and lower collimator widths were reduced to 0.030" and the x-ray generator operated at 40 kV, 1 mA. Thus, FIG. 25 shows a coincidence spectrum of scoring events for 150 μm sands falling in air. The TAC STARTs delayed by 2.6 ms, thus the mean correlation time was 3.7 ms. For example, the measured correlation peak was at about 1.1 ms, corresponding to a transient time of 3.7 ms between the two beams, and a sand velocity of 0.8 m/s. Smaller sand falls at a slower speed than larger ones possibly due to the drag in air. FIG. 26 shows the sanding signal width distribution for the nominal 150 μm sands falling in air with comparator's reference voltage set at near the DC level noise edge (e.g., the comparator's reference voltage was set at just below the noise). Both collimator openings were 750 μm×200 μm, respectively, and the x-ray source was at 40 kV, 1 mA. The most probable blocking time was at about 0.28 ms, which corresponds to about 120 μm. FIG. 27, shows the sanding signal width distributions for the nominal 150 μm sands falling in air with comparator's reference voltage set at 40 mV above the DC level. Both collimator openings were 300 μm×200 μm, respectively, and the x-ray source was at 21 kV, 1 mA. Thus, FIG. 27 shows a similar blocking time distribution for 150 μm sand but with 0.008"×0.12" collimator openings and with the x-ray tube at 21 kV, 1 mA.

The ratio of coincident to accidental events was about 1.55 in FIG. 21 and about 0.44 in FIG. 25. This reflects mainly the different coincidence probabilities for the two different collimator widths. The coincidence rate $R_c$ is given by:

$$R_c \approx \frac{1}{2} N \times P, \tag{10}$$

and the accidental rate $R_a$ is:

$$R_a \approx N^2 T, \tag{11}$$

where N is the rate of the scoring events at the input of either comparator, T is the TAC opening time (2 ms typical), and P is the scoring probability in the lower beam after a sand successfully scored in the upper beam. The factor ½ in eqn. (10) accounts for the fact that approximately half of the scoring events were in the lower beam and therefore not valid starts for TAC. The ratio of the coincidence events to accidental events is:

$$\frac{R_c}{R_a} \approx \frac{P}{2NT}. \tag{12}$$

We didn't record N in our experiment, but it can be estimated from eqn. (11). The accidental rate $R_a$ can be estimated from the measured TAC spectrum, which was about 7.5/sec for FIG. 21. It follows that N≈61 /sec, and from eqn. (12) we obtain P≈0.38.

For FIG. 25, $R_a \approx 25$/sec, and $R_c \approx 11$/sec. It follows that $N \approx 112$/sec and $P \approx 0.2$. Thus, by reducing the collimator openings widths by a factor of 4, from 0.12" to 0.03", we also cut the probability of correlated hits by a factor of almost two.

Figure 28:
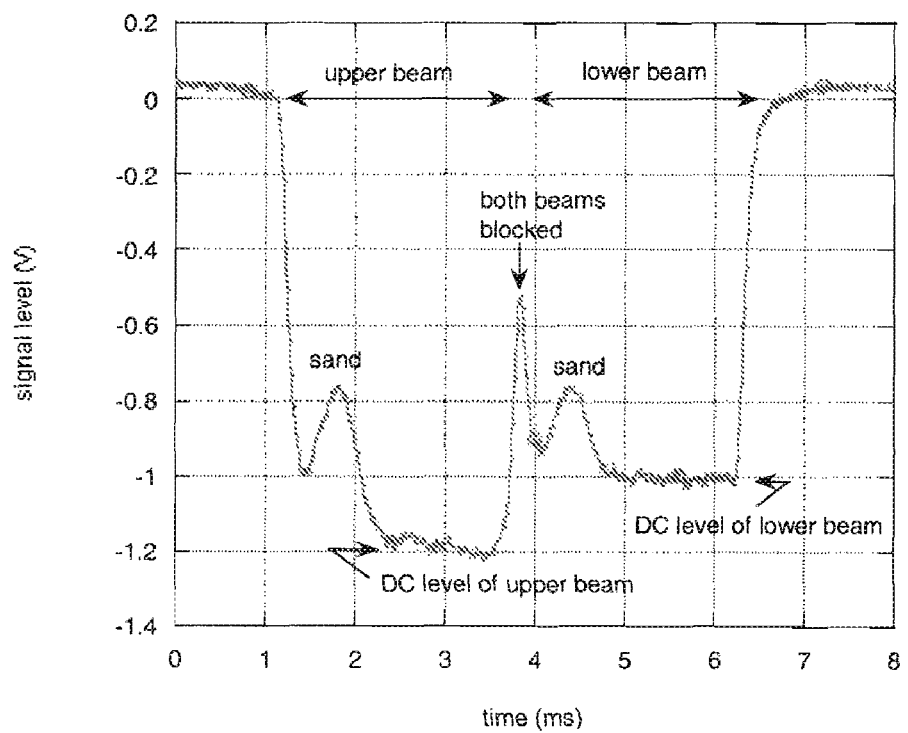
FIG. 28 illustrates a scope trace of a chopped x-ray beam with a mechanical shutter (slots cut on a rotating 1/16" thick Pb disk) according to an aspect of the invention.

FIG. 28 shows a scope trace of a chopped x-ray beam with a mechanical shutter (slots cut on a rotating 1/16" thick Pb disk).

Finally, we would like to point out that with a simple modification of the apparatus we can improve $R_c/R_a$ significantly. There are three types of events that contribute to $R_a$:
(1) A START signal from a lower beam score (a false START),
(2) A STOP signal from an upper beam score (a false STOP), and
(3) Uncorrelated accidental valid STARTs and STOPs.

The first two types of events can be eliminated completely if we associate scoring events with the originating x-ray beams by inserting a shutter between the detector collimator and the detector, as shown in FIG. 3. The shutter alternately opens one of the two openings but never at the same time. FIG. 28 is a scope trace obtained with such an arrangement. The shutter chops the DC beam into two successive pulses. The first pulse was associated with the upper beam and the second pulse was associated with the lower beam. The peak in the middle was the result of both collimator openings being blocked momentarily. There won't be any false START or STOP events if we gate comparators #1 and #2 with signals whose widths and timing coincide with the exposure times of the upper and lower beams, respectively.

This report presents the results of a proof-of-principle investigation of a simple, inexpensive and yet capable sand analyzing technique. The system uses a very low voltage x-ray generator (20-30 kV/1 mA) and a thin 1 mm conventional NaI detector coupled to a PMT. It detects sands in the flow line, measures the sand population and velocity, and provides an estimate of the grain size distribution. The sanding sensitivity is a function of the size of the target beam spot, the source energy, and the photon path length through the fluid. Our data suggest that one should be able to use this technique to analyze sands as small as 50 μm with a 20 keV end point energy x-ray beam through 6 mm of water. Reducing the x-ray path length in the fluid with an OFA-like cell, and/or increasing the beam current should further improve the sanding sensitivity. Although we demonstrated the technique with an x-ray source and detector, there is no reason why an optical source in the visible/UV/NIR range and a photo sensor shouldn't work, as long as both meet the requirements outlined in this report, especially if the fluid path length is reduced to 2 mm or less. Further, the technique also applies to detection of gas bubbles. The main difference between bubble detection and sand detection is that the signal polarity is reversed because gas bubbles has lower attenuation power than fluid.

Figure 29:
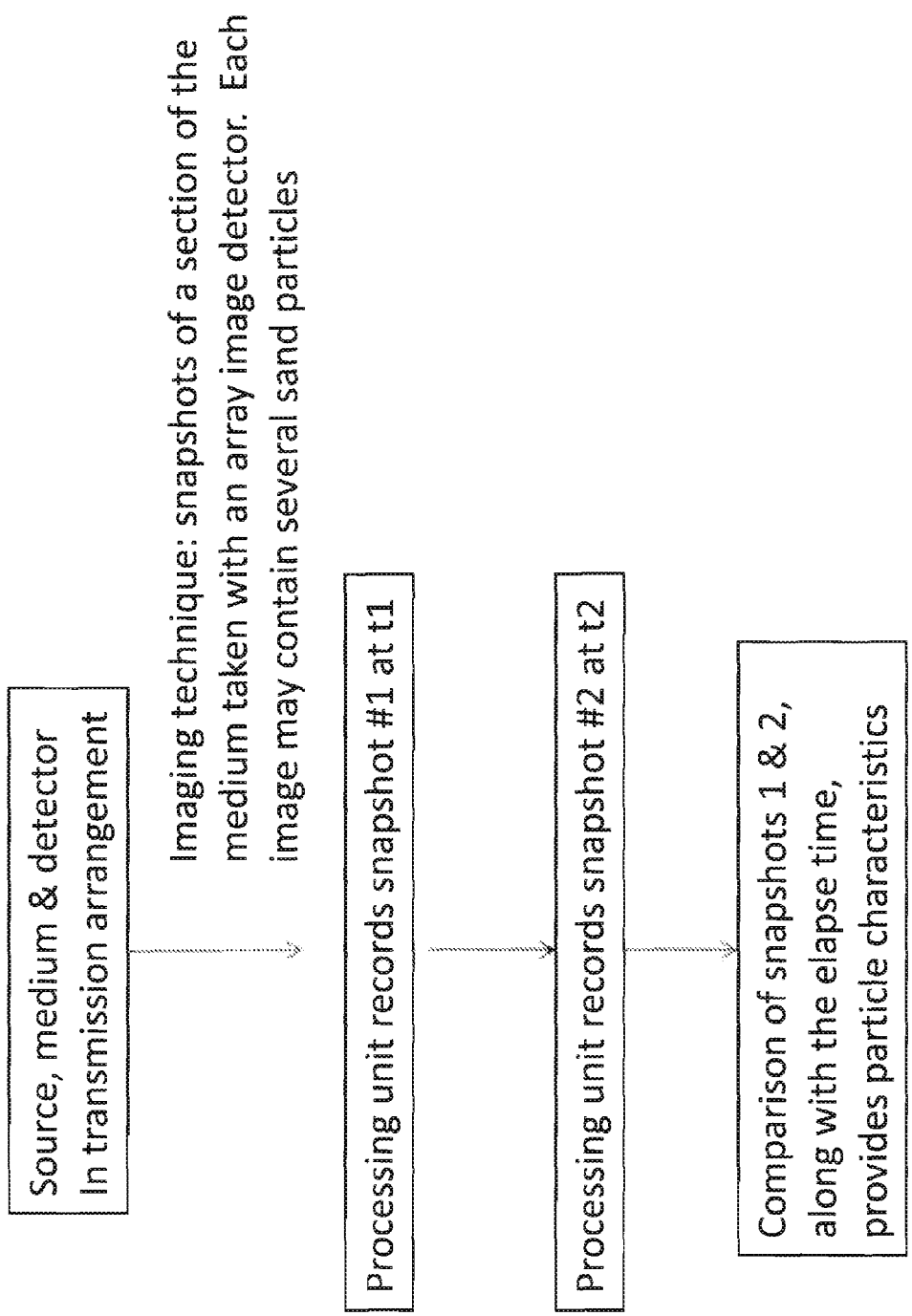
FIG. 29 illustrates a routine that may be used in implementing at least one embodiment of a method of the invention.

FIGS. 29 and 30 illustrates by non-limiting example, routines that may be used in implementing embodiments of methods of the invention.

Whereas many alterations and modifications of the present invention will no doubt become apparent to a person of ordinary skill in the art after having read the foregoing description, it is to be understood that the particular embodiments shown and described by way of illustration are in no way intended to be considered limiting. For example, methods of the invention allow for some steps of the method that are separated in time and/or space from other steps of the method. For example, in some embodiments, correlation of captured signal sequence representative of the particle profile may take place using a computer receiving a wireless signal. For example, such computer may be in a proximate operator's station or may be in a distant control center. Such wireless signals may be any signal capable of wirelessly relaying information, for example known wireless methods, traditional radio signals or telecommunications signals. Such signals may be transmitted continuously, intermittently and may include intervening transceivers which may relay the information wirelessly or via wires. The nature of the communications methods will vary in accordance with the particular application of the method or device. In some embodiments where band-width is limited, correlation does not take place remotely but the results are transmitted wirelessly to another location. Further, the invention has been described with reference to particular preferred embodiments, but variations within the spirit and scope of the invention will occur to those skilled in the art. It is noted that the foregoing examples have been provided merely for the purpose of explanation and are in no way to be construed as limiting of the present invention. While the present invention has been described with reference to an exemplary embodiment, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. An analyzing device for detecting particles in a fluid within a medium, the analyzing device comprising:
a source adapted to transmit a primary signal beam;
at least one detector, wherein (1) the at least one detector and the source are structured and arranged on opposite sides of the medium, (2) the analyzing device splits the primary signal beam into a first beam and a second beam that are each transmitted into the medium, and (3) the at least one detector is adapted to detect the first beam and the second beam transmitted through the medium; and
a processing unit in communication with the at least one detector and adapted to produce output signals representative of one of at least one individual particle characteristic or one or more individual particle property, wherein producing the output signals comprises measuring particle signal delays between the first beam and the second beam that are detected by the at least one detector.

2. The analyzing device of claim 1, wherein the at least one individual particle characteristic is from the group consisting of one of a particle velocity distribution, a particle size distribution, an average particle velocity, an average size of the particles, or a particle population.

3. The analyzing device of claim 1, wherein the at least one individual particle characteristic is a sand grain characteristic, such that the sand grain characteristic is from the group consisting of one of a sand grain velocity distribution, a sand grain size distribution, an average sand grain velocity, average size of the sand grains, a sand grain population, or a sand production rate as a function of a draw down pressure.

4. The analyzing device of claim 1, wherein the one or more individual particle property is from the group consisting of one of a particle size, a mean particle size, or particle shape.

5. The analyzing device of claim 1, wherein the one or more individual particle property is a sanding property from the group consisting of one of a sand grain size, a sand grain mean size, or a sand grain shape.

6. The analyzing device of claim 1, wherein the individual particles are one or more sand grains or gas bubbles.

7. The analyzing device of claim 1, wherein the analyzing device is capable of operating at least in an approximate temperature of at least 150° C.

8. The analyzing device of claim 1, wherein the analyzing device is capable of operating in one of a downhole environment, a subterranean environment or an oil field application.

9. The analyzing device of claim 1, wherein the source is a single x-ray source adapted to transmit x-ray signals and the at least one detector is an x-ray detector.

10. The analyzing device of claim 1, wherein the source includes one of a voltage x-ray tube or a light source with a wavelength.

11. The analyzing device of claim 10, wherein the voltage x-ray tube has an operating range approximately 20-30 kV with 1 mA target current.

12. The analyzing device of claim 1, wherein the at least one detector includes one of a NaI detector coupled to a PMT in operation with the source, such that the source is an x-ray source or a PMT having a photo-cathode operable with an optical source wavelength.

13. The analyzing device of claim 1, wherein the source includes an x-ray generator operable at approximately 30 kV with 1 mA target current.

14. The analyzing device of claim 1, wherein the medium is from the group consisting of one or more flow line, at least one pipe, one or more conduit, a tool device, a compartment within a device, a channel, or a wellbore.

15. The analyzing device of claim 1, wherein the at least one detector is a single detector.

16. The analyzing device of claim 1, wherein the detected particles are at least one particle having a size with an approximate range between 50 to 1000 microns.

17. The analyzing device of claim 1, wherein the fluid is one of moving, stimulated, or excited.

18. The analyzing device of claim 1, wherein the fluid has a fluid velocity up to approximately 100 feet per second.

19. The analyzing device of claim 1, further comprising at least one imaging device receiving output signals adapted to depict a plurality of signal sequences representative of the particle characteristics.

20. The analyzing device of claim 1, wherein the primary signal beam is a primary X-ray beam, the first beam is a first X-ray beam, and the second beam is a second X-ray beam.

21. The analyzing device of claim 20, wherein the individual particles are sand grains and the analyzing device is configured to measure one or more sand grain sizes and one or more sand grain velocities by measuring sanding signal delays between the first X-ray beam and the second X-ray beam independent of the medium orientation.

22. The analyzing device of claim 1, further comprising:
at least one collimator positioned between the source and the at least one detector.

23. An analyzing device for detecting particles in a fluid within a medium, such that one or more sampling module communicates the fluid from the medium into at least one analyzing module, the analyzing device comprising:
a source adapted to transmit a primary signal beam;
at least one detector, wherein (1) the at least one detector and the source are structured and arranged on opposite sides of the fluid, (2) the analyzing device splits the primary signal beam into a first beam and a second beam that are each transmitted into the fluid, and (3) the at least one detector is adapted to detect the first beam and the second beam transmitted through the fluid; and
at least one processing unit in communication with the at least one detector and adapted to produce a plurality of output signals representative of one of at least one individual particle characteristic or one or more individual particle property, wherein producing the output signals comprises measuring particle signal delays between the first beam and the second beam that are detected by the at least one detector.

24. The analyzing device of claim 23, wherein the one or more sampling module includes one of a channel, an intake device or a fluid intake channel or some combination thereof 25. The analyzing device of claim 24, wherein the fluid intake channel provides for evaluating one or more gravel pack.

26. The analyzing device of claim 23, wherein the one or more sampling module is one of a MDT probe, a portion of the MDT probe or a device capable of operating in an oil field application so as to extract at least one sample from the fluid.

27. The analyzing device of claim 26, wherein the MDT probe includes at least one pumping module capable of providing for one of at least one pressure measurement or extracting at least one sample of the fluid from a borehole wall.

28. The analyzing device of claim 23, wherein the at least one particle characteristic is from the group consisting of one of a particle velocity distribution, a particle size distribution, an average particle velocity, a particle size uniformity, or a particle population.

29. The analyzing device of claim 23, wherein the at least one particle characteristic is a sand grain characteristic, such that the sand grain characteristic is from the group consisting of one of a sand grain velocity distribution, a sand grain size distribution, an average sand grain velocity, averaging size of the sand grains, a sand grain size uniformity, a sand grain population, or a sand production rate as a function of a draw down pressure.

30. The analyzing device of claim 23, wherein the individual particles are sand grains.

31. The analyzing device of claim 23, wherein the one or more individual particle property is from the group consisting of one of a particle size, a mean particle size, or particle shape.

32. The analyzing device of claim 23, wherein the one or more individual particle property is a sanding property from the group consisting of one of a sand grain size, a sand grain mean size, or a sand grain shape.

33. The analyzing device of claim 23, wherein analyzing device is capable of operating at least in a temperature of 150° C.

34. The analyzing device of claim 23, wherein the analyzing device is capable of operating in one of a downhole environment, a subterranean environment or an oil field application.

35. The analyzing device of claim 23, wherein the source is a single x-ray source adapted to transmit x-ray signals and the at least one detector is an x-ray detector.

36. The analyzing device of claim 23, wherein the source includes one of a voltage x-ray tube or a light source with a wavelength.

37. The analyzing device of claim 36, wherein the voltage x-ray tube has an operating range of approximately 20-30 kV with 1 mA target current.

38. The analyzing device of claim 23, wherein the at least one detector includes a NaI detector coupled to a PMT in operation with the source, such that the source is an x-ray source or a PMT having a photo-cathode operable with an optical source wavelength.

39. The analyzing device of claim 23, wherein the source includes an x-ray generator operable at approximately 30 kV with 1 mA target current.

40. The analyzing device of claim 23, wherein the medium is from the group consisting of one or more flow line, at least one pipe, one or more conduit, a tool device, a compartment within a device, a channel, or a wellbore.

41. The analyzing device of claim 23, further comprising at least one imaging device receiving the output signal adapted to depict a signal sequence representation of the at least one individual particle characteristic or the one or more individual particle property.

42. The analyzing device of claim 23, wherein the primary signal beam is a primary X-ray beam, the first beam is a first X-ray beam, and the second beam is a second X-ray beam.

43. The analyzing device of claim 42, wherein the individual particles are sand grains and the analyzing device is configured to measure at least one sand grain size and one or more sand grain velocities by measuring sanding signal delays between the first X-ray beam and the second X-ray beam independent of the at least one analyzing module orientation.

44. The analyzing device of claim 23, further comprising:
at least one collimator positioned between the source and the at least one detector.

* * * * *